(12) United States Patent
Andruzzi et al.

(10) Patent No.: US 11,162,129 B2
(45) Date of Patent: Nov. 2, 2021

(54) PHOTOPROTECTIVE MIXTURES AS IMAGING REAGENTS IN SEQUENCING-BY-SYNTHESIS

(71) Applicant: IsoPlexis Corporation, Branford, CT (US)

(72) Inventors: Luisa Andruzzi, Concord, MA (US); Michel Georges Perbost, Belmont, MA (US); Dona Hevroni, Lexington, MA (US); Minakshi Guha, Wakefield, MA (US); Austin Ricker, Waltham, MA (US); Timothy Pelletier, Fitchburg, MA (US)

(73) Assignee: IsoPlexis Corporation, Branford, CT (US)

( * ) Notice: Subject to any disclaimer, the term of this patent is extended or adjusted under 35 U.S.C. 154(b) by 450 days.

(21) Appl. No.: 15/799,139

(22) Filed: Oct. 31, 2017

(65) Prior Publication Data
US 2018/0127809 A1    May 10, 2018

Related U.S. Application Data

(60) Provisional application No. 62/419,702, filed on Nov. 9, 2016.

(51) Int. Cl.
| | |
|---|---|
| *C12Q 1/68* | (2018.01) |
| *C12Q 1/6806* | (2018.01) |
| *C12Q 1/6816* | (2018.01) |
| *C07C 215/28* | (2006.01) |
| *C07D 311/66* | (2006.01) |
| *C12Q 1/6874* | (2018.01) |
| *G01N 33/58* | (2006.01) |

(52) U.S. Cl.
CPC .......... *C12Q 1/6806* (2013.01); *C07C 215/28* (2013.01); *C07D 311/66* (2013.01); *C12Q 1/6816* (2013.01); *C12Q 1/6874* (2013.01); *G01N 33/582* (2013.01); *C07B 2200/07* (2013.01)

(58) Field of Classification Search
None
See application file for complete search history.

(56) References Cited

U.S. PATENT DOCUMENTS

| | | | |
|---|---|---|---|
| 3,817,837 A | 6/1974 | Rubenstein et al. | 435/7.9 |
| 3,850,752 A | 11/1974 | Schuurs et al. | 435/7.93 |
| 3,939,350 A | 2/1976 | Kronick et al. | 250/365 |
| 3,996,345 A | 12/1976 | Ullman et al. | 436/537 |
| 4,275,149 A | 6/1981 | Litman et al. | 435/7.91 |
| 4,277,437 A | 7/1981 | Maggio | 422/401 |
| 4,366,241 A | 12/1982 | Tom et al. | 435/7.91 |
| 4,683,195 A | 7/1987 | Mullis et al. | 435/6.11 |
| 4,683,202 A | 7/1987 | Mullis | 435/91.2 |
| 6,664,079 B2 | 12/2003 | Ju et al. | 435/91.1 |
| 8,999,674 B2 * | 4/2015 | Beechem | C07H 19/20 435/91.1 |
| 9,145,589 B2 * | 9/2015 | Gordon | B01L 3/502761 |
| 2006/0183798 A1 | 8/2006 | Cavazza et al. | 514/183 |
| 2015/0079603 A1 | 3/2015 | Yue et al. | 424/9.6 |

OTHER PUBLICATIONS

Dean et al. (Nature Chemical Biology, 2014, vol. 10: 512-523) (Year: 2014).*
Raza et al. (Bioorganic & Medicinal Chemistry Letters, 2013, vol. 23:620-623) (Year: 2013).*
Vanella et al. (Cell Biology and Toxicology, 2000, 16:99-104) (Year: 2000).*
Esmaeili et al. (Clin and Exper Pharmacol and Physiol, 2014, 41:416-422) (Year: 2014).*
Sharma et al. (J of Botany, 2012, article ID 217037, p. 1-26) (Year: 2012).*
Anderson, M. L. M. et al. (1985) "Quantitative Filter Hybridization," in *Nucleic Acid Hybridisation: A Practical Approach* (Hames, B. D., et al., Eds.), pp. 73-111, Oxford University Press, USA.
Dieffenbach, C. W. et al. (1995) *PCR Primer, A Laboratory Manual*, Cold Spring Harbor Laboratory Press, Plainview, N.Y.
PCT International Search Report of International Application No. PCT/US2017/059318 dated Mar. 7, 2018.

* cited by examiner

*Primary Examiner* — Stephanie K Mummert
(74) *Attorney, Agent, or Firm* — Cooley LLP; Ivor R. Elrifi; Brian P. Hopkins

(57) ABSTRACT

The invention relates to methods, compositions, devices, systems and kits as described including, without limitation, reagents and mixtures for determining the identity of nucleic acids in nucleotide sequences using, for example, sequencing by synthesis methods. In particular, the present invention contemplates the use of photoprotective mixture of compounds as imaging reagents to improve stability and storage of fluorescent compounds, including but not limited to, nucleotides with fluorescent labels.

10 Claims, 19 Drawing Sheets

PHOTOPROTECTIVE MIXTURES AS IMAGING REAGENTS IN SEQUENCING-BY-SYNTHESIS

RELATED APPLICATIONS

This application claims priority to, and the benefit of, U.S. Provisional Application No. 62/419,702, filed on Nov. 9, 2016, the entire contents of which are hereby incorporated by reference.

FIELD OF THE INVENTION

The invention relates to methods, compositions, devices, systems and kits as described including, without limitation, reagents and mixtures for determining the identity of nucleic acids in nucleotide sequences using, for example, sequencing by synthesis methods. In particular, the present invention contemplates the use of photoprotective mixture of compounds as imaging reagents to improve stability and storage of fluorescent compounds, including but not limited to, nucleotides with fluorescent labels.

BACKGROUND

Over the past 25 years, the amount of DNA sequence information that has been generated and deposited into Genbank has grown exponentially. Traditional sequencing methods (e.g., for example Sanger sequencing) are being replaced by next-generation sequencing technologies that use a form of sequencing by synthesis (SBS), wherein specially designed nucleotides and DNA polymerases are used to read the sequence of chip-bound, single-stranded DNA templates in a controlled manner. To attain high throughput, many millions of such template spots are arrayed across a sequencing chip and their sequence is independently read out and recorded.

Systems for using arrays for DNA sequencing are known (e.g., Ju et al, U.S. Pat. No. 6,604,079). However, there is a continued need for methods and compositions for increasing the efficiency and/or reagent stability for sequencing nucleic acid sequences with automated sequencing.

SUMMARY OF THE INVENTION

The invention relates to methods, compositions, devices, systems and kits as described including, without limitation, reagents and mixtures for determining the identity of nucleic acids in nucleotide sequences using, for example, sequencing by synthesis methods. In particular, the present invention contemplates the use of photoprotective reagent mixture of compounds as imaging reagents to improve stability and storage of fluorescent compounds, including but not limited to, nucleotides with fluorescent labels.

In one embodiment, the present invention contemplates a photoprotective mixture (e.g., a cocktail) of compounds as an imaging reagent during a fluorophore detection step following nucleotide incorporation in sequencing-by-synthesis (SBS). In one embodiment, the photoprotective mixture comprises at least one effective antioxidant such as, but not limited to, 2,5-dihydrobenzoic acid (gentisic acid); 3,4-dihydroxybenzoic acid (protocatechuic acid) or 3,4-dihydroxybenzoic acid ethyl ester (protocatechuate ethyl ester), at least one fluorescence quenching inhibitor such as, but not limited to, 6-hydroxy-2,5,7,8-tetramethylchromane-2-carboxylic acid (trolox) and at least one radical scavenger such as, but not limited to, carnitine.

In one embodiment, the present invention contemplates, a method of incorporating labeled nucleotides, comprising: a) providing; i) a plurality of nucleic acid primers and template molecules, ii) a polymerase, iii) an imaging reagent comprising a photoprotective mixture of compounds, and iv) a plurality of nucleotide analogues wherein at least a portion of said nucleotide analogues is labeled with a label attached through a cleavable linker to the base; b) hybridizing (e.g., under high stringency) at least a portion of said primers to at least a portion of said template molecules so as to create hybridized primers; c) incorporating a first labeled nucleotide analogue with said polymerase into at least a portion of said hybridized primers so as to create extended primers comprising an incorporated labeled nucleotide analogue; and d) imaging said incorporated labeled nucleotide analogue in the presence of said imaging reagent. In one embodiment, the imaging reagent comprises a fluorescence quenching inhibitor. In one embodiment, the fluorescence quenching inhibitor is trolox. In one embodiment, the photoprotective mixture comprises at least one antioxidant, at least one quenching inhibitor and at least one radical scavenger compound. In one embodiment, the antioxidant is selected from the group consisting of gentisic acid, protocatechuic acid and protocatechuate ethyl ester. In one embodiment, the radical scavenger compound is carnitine. In one embodiment, the method further comprises: e) incorporating a second nucleotide analogue with said polymerase into at least a portion of said extended primers. In one embodiment, the label is fluorescent.

In one embodiment, the present invention contemplates an imaging reagent comprising at least one antioxidant, at least one fluorescence quenching inhibitor and a buffer. In one embodiment, the antioxidant comprises compounds selected from the group consisting of gentisic acid, protocatechuic acid and protocatechuate ethyl ester. In one embodiment, the imaging reagent further comprises a radical scavenger. In one embodiment, the radical scavenger is carnitine. In one embodiment, the fluorescence quenching inhibitor is trolox, one embodiment, the buffer is a TRIS buffer. In one embodiment, the buffer is a HEPES buffer.

In one embodiment, the present invention contemplates a kit, comprising i) a first container comprising an imaging reagent comprising at least one antioxidant, at least one fluorescence quenching inhibitor and a buffer; and ii) a second container comprising a plurality of nucleotide analogues wherein at least a portion of said nucleotide analogues is labeled with a label attached through a cleavable linker to the base. In one embodiment, the imaging reagent further comprises a radical scavenger. In one embodiment, the radical scavenger is carnitine. In one embodiment, the fluorescence quenching inhibitor is trolox. In one embodiment, the buffer is a TRIS buffer. In one embodiment, the buffer is a HEPES buffer.

In one embodiment, the present invention contemplates a system comprising a solution of primers hybridized to a template comprising a plurality of nucleotide analogues attached to a cleavable label and an imaging reagent comprising at least one antioxidant, at least one fluorescent quenching inhibitor and a buffer. In one embodiment, the hybridized primers and said template are immobilized. In one embodiment, the hybridized primers and said template are in a flow cell. In one embodiment, the imaging reagent further comprises a radical scavenger. In one embodiment, the radical scavenger is carnitine. In one embodiment, the fluorescence quenching inhibitor is trolox. In one embodiment, the buffer is a TRIS buffer. In one embodiment, the buffer is a HEPES buffer.

In one embodiment, the present invention contemplates an imaging reagent comprising: i) a TRIS HCl buffer; ii) carnitine ranging in concentration between approximately 5-50 mM; iii) trolox ranging in concentration between approximately 5-15 mM; iv) 2,5 dihydroxybenzoic acid ranging in concentration between approximately 10-50 mM; and v) 3,4, dihydroxybenzoic acid ethyl ester ranging in concentration between approximately 10-20 mM.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but also plural entities and also includes the general class of which a specific example may be used for illustration. The terminology herein is used to describe specific embodiments of the invention, but their usage does not delimit the invention, except as outlined in the claims.

The term "about" as used herein, in the context of any of any assay measurements refers to +/−5% of a given measurement.

The term "imaging reagent" as used herein, refers to a mixture of compounds that are capable of enhancing label emission intensity and/or improving fluorophore detection by at least an order of magnitude. While not intending to limit the invention to any particular mechanism, it is believed that the herein described mixtures enhance signal-to-noise ratios, or reduce photobleaching and/or fluorophore "blinking." One class of compounds that are useful in imaging reagents are fluorescence quenching inhibitors.

The term "fluorescence quenching inhibitor" as used herein, refer to a class of compounds that improve the signal quality of fluorescent labels. Without being bound to any mechanism, it is believed that such compounds work by reacting with oxidation compounds that result in a quenching of the fluorescent signal by non-specific photo-bleaching phenomenon. For example, one such compound is trolox (6-hydroxy-2,5,7,8-tetramethylchroman-2-carboxylic acid).

The term "mixture" or "cocktail" as used herein interchangeably, refers to a plurality of compounds (generally in a solution, such as a buffer solution) that together create an imaging reagent for the purpose of detecting labeled nucleotide analogues within a nucleotide sequence.

The term "photoprotective" as used herein, refers to an end result of an imaging reagent mixture or cocktail that enhances stability and storage shelf-life of fluorescent compounds. Without being bound by theory, it is believed that they work by protecting against: i) photo-bleaching of nucleotide fluorescent labels; ii) signal quenching; and iii) radically-induced DNA photo-damage and photo-scission.

The term "antioxidant compounds" as used herein, refers to a molecule that inhibits a chemical reaction that can produce free radicals. For example, many vitamins (e.g., vitamin E and vitamin C), in addition to certain enzymes (catalase and superoxide dismutase) are naturally occurring antioxidants. Other chemicals also have these properties including, but not limited to, gentisic acid, protocatechuic acid and/or protocatechuate ethyl ester.

The term "radical scavenger compound" as used herein, refers to a molecule that remove or de-activate impurities and unwanted reaction products, for example oxygen. While radical scavenger compounds have an antioxidant end result, it is believed that they function by a different mechanism than antioxidant compounds. For example, one such radical scavenger compound includes, but is not limited to, tocopherol, carnitine and/or naringenin. Even so, it is known that some radical scavenger compounds have other biochemical activities, for example, antioxidant activities and singlet oxygen quenching.

The term "buffer" as used herein, refers to a mixture of basic salts and a hydrogen exchange compound (either a weak acid or a weak base) that can maintain a stable pH level over a wide range of environmental conditions (e.g., temperature, salinity), including changes in hydrogen ion concentration. For example, such buffers may include, but are not limited to 4-(2-hydroxyethyl)-1-piperazineethanesulfonic acid (HEPES) buffer and/or tris(hydroxymethyl)-aminomethane (TRIS) buffer.

The term "linker" as used herein, refers to any molecule (or collection of molecules) capable of attaching a label and/or chemical moiety that is susceptible to cleavage. In one embodiment, cleavage of the linker may produce toxic radical products. For example, a linker may include, but is not limited to, a disulfide linker and/or an azide linker.

The term "attached" as used herein, refers to any interaction between a first molecule (e.g., for example, a nucleic acid) and a second molecule (e.g., for example, a label molecule). Attachment may be reversible or irreversible. Such attachment includes, but is not limited to, covalent bonding, ionic bonding, Van der Waals forces or friction, and the like.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand. Such nucleic acids may include, but are not limited to, cDNA, mRNA or other nucleic acid sequences.

The term "an isolated nucleic acid", as used herein, refers to any nucleic acid molecule that has been removed from its natural state (e.g., removed from a cell and is, in a preferred embodiment, free of other genomic nucleic acid).

In some embodiments, the present invention contemplates hybridizing nucleic acid together. This requires some degree of complementarity. As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A," Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarily between nucleic acid strands has significant effects on the efficiency and strength of hybridization between nucleic acid strands. This is of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e. identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

Low stringency conditions comprise conditions equivalent to binding or hybridization at 42° C. in a solution consisting of 5×SSPE (43.8 g/l NaCl, 6.9 g/l NaH2PO4.H2O and 1.85 g/l EDTA, pH adjusted to 7.4 with NaOH), 0.1% SDS, 5×Denhardt's reagent {50×Denhardt's contains per 500 ml: 5 g Ficoll (Type 400, Pharmacia), 5 g BSA (Fraction V; Sigma)} and 100 µg/ml denatured salmon sperm DNA followed by washing in a solution comprising 5× SSPE, 0.1% SDS at 42° C. when a probe of about 500 nucleotides in length, is employed. Numerous equivalent conditions may also be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g. the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) may also be used.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the Tm of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., C0 t or R0 t analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "Tm" is used in reference to the "melting temperature." The melting temperature is the temperature at which a population of double-stranded nucleic acid molecules becomes half dissociated into single strands. As indicated by standard references, a simple estimate of the Tm value may be calculated by the equation: $Tm=81.5+0.41$ (% G+C), when a nucleic acid is in aqueous solution at 1M NaCl. Anderson et al., "Quantitative Filter Hybridization" In: Nucleic Acid Hybridization (1985). More sophisticated computations take structural, as well as sequence characteristics, into account for the calculation of Tm.

As used herein the term "stringency" is used in reference to the conditions of temperature, ionic strength, and the presence of other compounds such as organic solvents, under which nucleic acid hybridizations are conducted, "Stringency" typically occurs in a range from about Tm to about 20° C. to 25° C. below Tm. A "stringent hybridization" can be used to identify or detect identical polynucleotide sequences or to identify or detect similar or related polynucleotide sequences. For example, when fragments are employed in hybridization reactions under stringent conditions the hybridization of fragments which contain unique sequences (i.e., regions which are either non-homologous to or which contain less than about 50% homology or complementarity) are favored. Alternatively, when conditions of "weak" or "low" stringency are used hybridization may occur with nucleic acids that are derived from organisms that are genetically diverse (i.e., for example, the frequency of complementary sequences is usually low between such organisms).

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" or (more simply) "template" refers to nucleic acid originating from a sample which is analyzed for the presence of a target sequence of interest. In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

"Amplification" is defined as the production of additional copies of a nucleic acid sequence and is generally carried out using polymerase chain reaction. Dieffenbach C. W. and G. S. Dveksler (1995) In: PCR Primer, a Laboratory Manual, Cold Spring Harbor Press, Plainview, N.Y.

As used herein, the term "polymerase chain reaction" ("PCR") refers to the method of K. B. Mullis U.S. Pat. Nos. 4,583,195 and 4,683,202, herein incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". With PCR, it is possible to amplify a single copy of a specific target sequence in genomic DNA to a level detectable by several different methodologies (e.g., hybridization with a labeled probe; incorporation of biotinylated primers followed by avidin enzyme conjugate detection; incorporation of 32P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxy-ribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers; to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "label" or "detectable label" are used herein, to refer to any composition detectable by spectroscopic, photochemical, biochemical, immunochemical, electrical, optical or chemical means. Such labels include biotin for staining with labeled, streptavidin conjugate, magnetic beads (e.g., Dynabeads®), fluorescent dyes (e.g., fluorescein, texas red, rhodamine, green fluorescent protein, and the like), radiolabels (e.g., 3H, 125I, 35S, 14C, or 32P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include, but are not limited to, U.S. Pat. Nos. 3,817,837; 3,850,752; 3,939,350; 3,996,345; 4,277, 437; 4,275,149; and 4,366,241 (all herein incorporated by reference).

In a preferred embodiment, the label is typically fluorescent and is linked to the base of the nucleotide. For cytosine and thymine, the attachment is usually to the 5-position. For the other bases, a deaza derivative is created and the label is linked to a 7-position of deaza-adenine or deaza-guanine.

The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

The term "luminescence" and/or "fluorescence", as used herein, refers to any process of emitting electromagnetic radiation (light) from an object, chemical and/or compound. Luminescence and/or fluorescence results from a system which is "relaxing" from an excited state to a lower state with a corresponding release of energy in the form of a photon. These states can be electronic, vibronic, rotational, or any combination of the three. The transition responsible for luminescence can be stimulated through the release of energy stored in the system chemically or added to the system from an external source. The external source of energy can be of a variety of types including, but not limited to, chemical, thermal, electrical, magnetic, electromagnetic, physical or any other type capable of causing a system to be excited into a state higher than the ground state. For example, a system can be excited by absorbing a photon of light, by being placed in an electrical field, or through a chemical oxidation-reduction reaction. The energy of the photons emitted during luminescence can be in a range from low-energy microwave radiation to high-energy x-ray radiation. Typically, luminescence refers to photons in the range from UV to IR radiation.

BRIEF DESCRIPTION OF THE FIGURES

FIG. 1A: An illustrative workflow for a conventional imaging buffer kit configuration.

FIG. 1B: A photoprotective imaging buffer kit configuration comprising new and improved Cleave and Imaging Buffer Consumables.

FIG. 3A: Run 8.3
FIG. 3B: Run 8.5
FIG. 3C: Run 8.6
FIG. 3D: Run 8.41 (retest)

FIG. 4A: Run 8.3
FIG. 4B: Run 8.5
FIG. 4C; Run 8.6
FIG. 4D: Run 8.41 (retest)

FIG. 6A: Photoprotective imaging buffer SC-P 9.
FIG. 6B: Photoprotective imaging buffer SC-P 9B.

FIG. 6C: Photoprotective imaging buffer SC-P 9C.

FIG. 9A Results using a HEPES buffer.

FIG. 9B: Results using a TRI S buffer.

FIG. 14A: SC-9 IB and SC9B IB versus reference IB.

FIG. 14B: SC-9D IB versus reference IB.

FIG. 15A: SC-9 IB and SC9B IB versus reference IB.

FIG. 15B: SC-9D IB versus reference IB.

DETAILED DESCRIPTION OF THE INVENTION

Figure 1A:
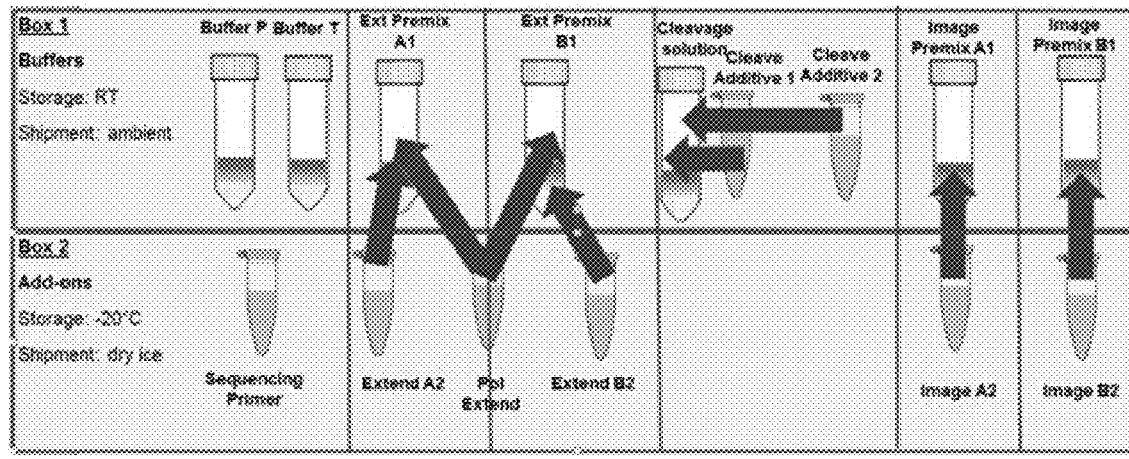
FIG. 1A-B presents a comparative workflow between a conventional imaging buffer configuration and photoprotective imaging buffer configuration.

The invention relates to methods, compositions, devices, systems and kits as described including, without limitation, reagents and mixtures for determining the identity of nucleic acids nucleotide sequences using, for example, sequencing by synthesis methods. In particular, the present invention contemplates the use of photoprotective buffer mixture of compounds as imaging reagents to improve stability and storage of fluorescent compounds, including but not limited to, nucleotides with fluorescent labels.

In one embodiment, the present invention contemplates compositions comprising photoprotective mixtures as imaging reagents during sequencing-by-synthesis (SBS). In one embodiment, a method comprising imaging occurs during a fluorophore detection step. In one embodiment, a method comprising imaging occurs following nucleotide incorporation. In one embodiment, a photoprotective mixtures comprises compounds such as, but not limited to: carnitine; 6-hydroxy-2,5,7,8-tetramethylchromane-2-carboxylic Acid (trolox); 2,5-dihydroxybenzoic acid (gentisic acid); 3,4-dihydroxybenzoic acid (protocatechuic acid); 3,4-dihydroxybenzoic acid ethyl ester (protocatechuate ethyl ester), 4-hydroxycinnamic acid, 3,4-dihydroxybenzeneacrylic acid, 1,4-diazabicyclo[2.2.2]octane (DABCO), lipoic acid and/or acetyl-carnitine.

In one embodiment, the present invention contemplates a method for sequencing a 150 bp read length. Other significant additional benefits are also provided including, but not limited to: improved manufacturing, storage and quality control processes, improved usability through user friendly kit concept and workflow, improved instrument reliability due to delivery of a single component solution that does not require mixing of individual components through next generation sequencing platform fluidics.

I. Sequencing-By-Synthesis (SBS)

In one embodiment, the present invention contemplates a series of method steps performed by an automated sequencing by synthesis instrument (e.g., a next generation sequencing platform). See U.S. Pat. No. 9,145,589, hereby incorporated by reference. In one embodiment, the instrument is comprised of numerous reagent reservoirs. Each reagent reservoir has a specific reactivity reagent dispensed within the reservoir to support the SBS process, for example:

In one embodiment, the SBS method comprises doing different steps at different stations. By way of example, each station is associated with a particular step. While not limited to particular formulations, some examples for these steps and the associated reagents are shown below:

1) Extend A Reagent: Comprises reversibly terminated labeled nucleotides and polymerase. One composition of Extend A may be as follows:

| Component | Concentration |
| --- | --- |
| PNSE (% wt/vol) | 0.005% |
| Tris × HCl (pH 8.8), mM | 50 |
| NaCl (mM) | 50 |
| EDTA (mM) | 1 |
| MgSO4 (mM) | 10 |
| Cystamine (mM) | 1 |
| Glycerol (% wt/vol) | 0.01% |
| Therminator IX* (U/ml) | 10 |
| N3-dCTP (μM) | 3.83 |
| N3-dTTP (μM) | 3.61 |
| N3-dATP (μM) | 4.03 |
| N3-dGTP (μM) | 0.4 |
| Alexa488-dCTP (nM) | 550 |
| R6G-dUTP (nM) | 35 |
| ROX-dATP (nM) | 221 |
| Cy5-dGTP (nM) | 66 |

*with Alkylated free Cysteine

2) Extend B Reagent: Comprises reversibly terminated unlabeled nucleotides and polymerase, but lacks labeled nucleotide analogues. One composition of Extend B may be as follows:

| Component | Concentration |
| --- | --- |
| PNSE (% wt/vol) | 0.005% |
| Tris × HCl (pH 8.8), mM | 50 |
| NaCl (mM) | 50 |
| EDTA (mM) | 1 |
| MgSO4 (mM) | 10 |
| Glycerol (% wt/vol) | 0.01% |
| Therminator IX* (U/ml) | 10 |
| N3-dCTP (μM) | 21 |
| N3-dTTP (μM) | 17 |
| N3-dATP (μM) | 21 |
| N3-dGTP (μM) | 2 |

*Alkylated free Cysteine

3) Wash solution 1 with a detergent (e.g., polysorbate 20) citrate buffer (e.g., saline)
4) Cleave Reagent: One cleaving solution composition may be as follows:

| Component | Concentration |
|---|---|
| NaOH (mM) | 237.5 |
| TrisHCl (pH 8.0) (mM) | 237.5 |
| TCEP (mM) | 50 |

5) Wash solution 2 with a detergent (e.g., polysorbate 20) a tris(hydroxymethyl)-aminomethane (Tris) buffer.

II. Conventional Imaging Solutions

One enzymatic formulation currently being used as an imaging reagent (IB) comprises four-components. These four components comprise HEPES buffer, glucose oxidase, glucose and trolox and are required to be combined to create two separate solutions prior to supporting an SBS method. These two solutions are kept separate throughout the sequencing process to prevent glucose oxidase and glucose from reacting prematurely with oxygen causing degradation of the enzymatic system and elimination of $H_2O_2$. These two final solutions are mixed during SBS through a mixing valve at every imaging step before introduction into a flow cell. Use of this type of imaging method step, albeit effective, presents challenges in several areas including, but not limited to: i) stability of the manufacturing process; ii) maintaining quality control due to complicated exo/endo specification paradigms; iii) difficult usability due to a complex kit configuration and workflow; iv) limited instrument reliability due to delivery volume failure modes due to mixing valve reliability issues. As seen herein, the conventional or baseline imaging reagent (IB) has been used for performance benchmarking of various embodiments of the presently disclosed photoprotective mixture imaging reagents.

III. Photoprotective Imaging Solutions

In one embodiment, effective imaging solutions and buffer formulations for SBS methods comprise molecular components that ensure photoprotection during light exposure. While not bound by theory, it is believed that they prevent three main phenomena: i) photo-bleaching of nucleotide fluorescent labels; ii) signal quenching; and iii) radically-induced DNA photo-damage and photo-scission. Imaging solutions can be formulated either as either enzymatic systems or mixtures comprising a variety of chemical mixtures such as mixtures including, but not limited to, a molecular oxygen "sink", an antioxidant/radical scavenger and a singlet oxygen quencher. Some of the components in these mixtures also provide additional protection against oxidative stress and degradation of the imaging solution upon prolonged storage.

Although it is not necessary to understand the mechanism of an invention it is believed that a "mixture" or "cocktail" approach is most suitable for formulating long shelf-life imaging solutions because it best supports a variety of functional aspects pertaining to product design robustness, ranging from functional performance and formulation stability to manufacturability, usability and storage.

In one embodiment, the present invention contemplates a photoprotective mixture as an imaging reagent during a fluorophore detection step following nucleotide incorporation in sequencing-by-synthesis (SBS). These photoprotective mixture imaging reagents comprise an effective antioxidant such as, but not limited to, 2,5-dihydroxybenzoic acid (gentisic acid); 3,4-dihydroxybenzoic acid (protocatechuic acid) or 3,4-dihydroxybenzoic acid ethyl ester (protocatechuate ethyl ester), a fluorescence quenching inhibitor such as, but not limited to, 6-hydroxy-2,5,7,8-tetramethylchromane-2-carboxylic acid (trolox) and a radical scavenger (e.g., carnitine), an antioxidant and/or a singlet oxygen quencher.

In one embodiment, the photoprotective cocktail comprises a mixture (e.g., imaging reagent SC-P 7B) including the components:

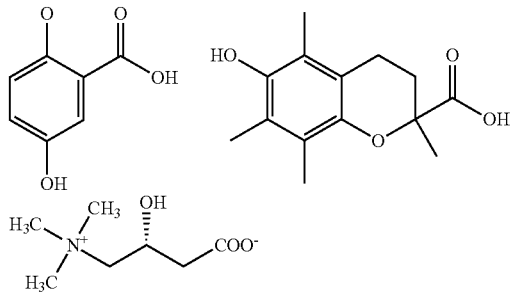

In one embodiment, the photoprotective cocktail comprises a mixture (e.g., imaging reagent SC-P 9C) including the components:

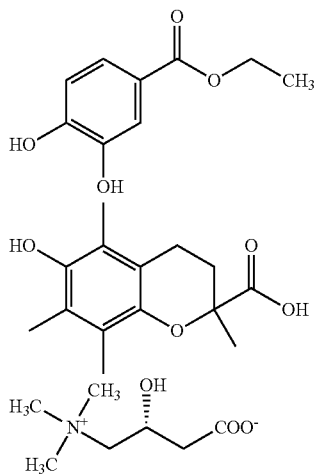

Photoprotective cocktail mixtures, exemplified by those above, have been designed with properties including, but not limited to, photoprotection, stability, manufacturability, long shelf life storage and usability. These mixtures are also designed for compatibility with off the shelf sequencing kits (i.e., the GeneReader® 1.1 sequencing kit). In particular, carnitine has been bound to induce reduction of oxidative stress and preservation of chemical activity and/or biological function after long term storage of biological fluids and functional buffers. Without being bound by theory, carnitine can conceivably support enhanced storage of complex molecular mixtures due to reduction of oxidative stress caused by molecules including, but not limited to, oxygen, peroxy radicals, or singlet oxygen. Although it is not necessary to understand the mechanism of an invention, it is believed that compounds such as carnitine preserve their protective properties, even upon prolonged storage as a formulation, including but not limited to molecular reduced states and stability against chemical bond scission (e.g., radical- or photo-scission).

The data presented herein demonstrates an interrogation potential for various photoprotective imaging mixtures of compounds as imaging reagents. Additionally, full compatibility with SBS instrument hardware is verified for all components as observed from an inspection of both instrument and liquid waste at the end of sequencing. Improvements of the presently disclosed photoprotective mixture imaging reagents are exemplified with comparative sequencing workflows.

Figure 1B:
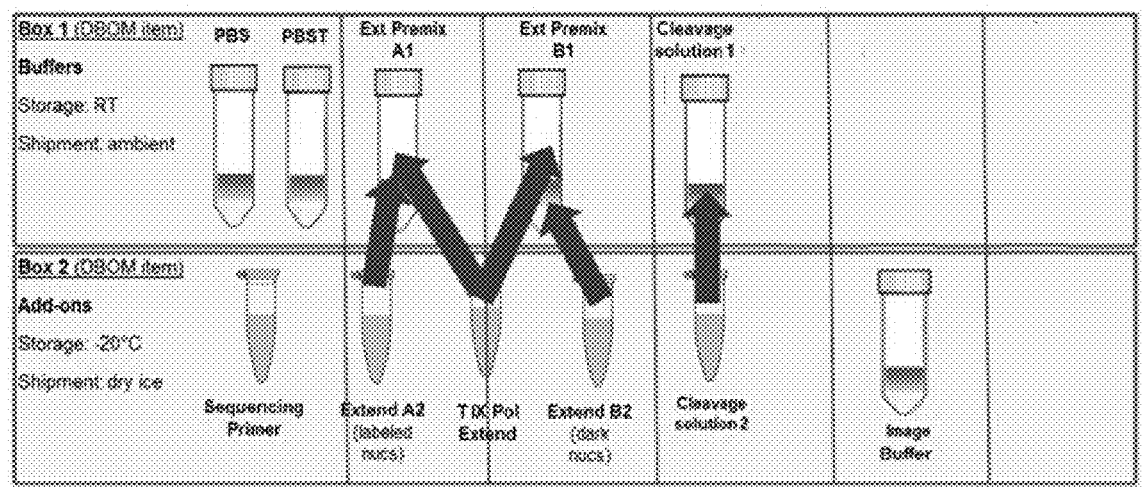

For example, a prospective kit configuration for photoprotective mixture imaging reagents is shown as a single component consumable stored in a kit box compatible with −20° C. storage conditions. See, FIG. 1A-B. An comparative workflow for a conventional imaging reagent kit configuration (FIG. 1A) demonstrates the increased complexity as opposed to the presently disclosed photoprotective imaging reagent kit configuration (FIG. 1B). Although it is not necessary to understand the mechanism of an invention, it is believed that the presently disclosed photoprotective imaging reagent kit configuration greatly improves usability during an SBS method by decreasing the number of components required in the kit and workflow.

Photoprotective imaging reagents as contemplated by the present invention have been tested for long read length sequencing performance (e.g., approximately 150 bp). Some of these tests entailed 157 cycle sequencing and a head-to-head comparison of photoprotective mixture imaging reagents to a conventional imaging reagent (e.g., baseline IB reagent). Studies were performed using Gene Reader instruments and two types of DNA libraries, i.e., NA12878/101X gene panel and NA12878/BRCA gene panel. Sequencing metrics were analyzed to provide comparative system performance indicators, e.g., raw error rate, average read length, output (Gb).

Figure 2:
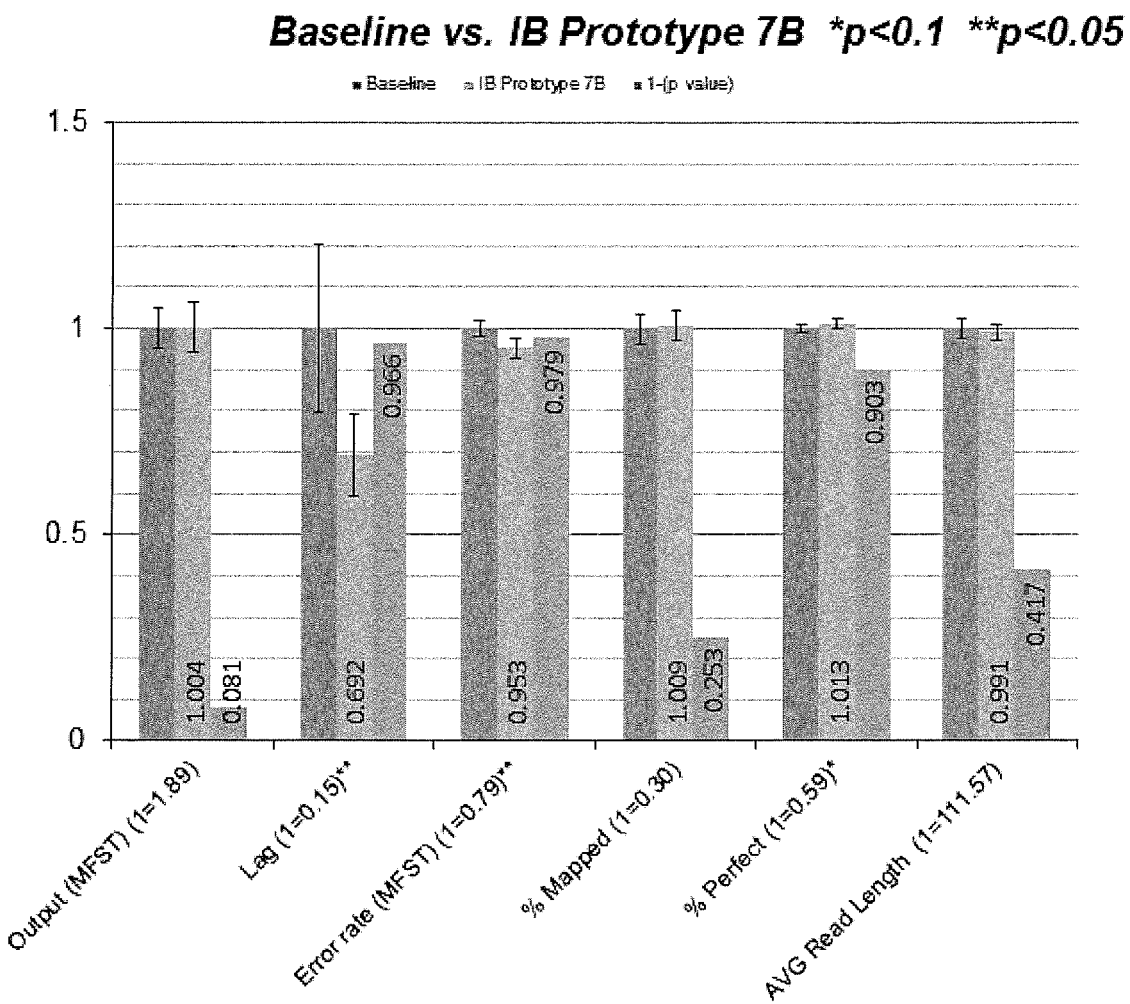
FIG. 2 presents exemplary data showing that SBS metrics are comparable between a conventional imaging buffer and a Photoprotective imaging buffer 7B.
Figure 3A:
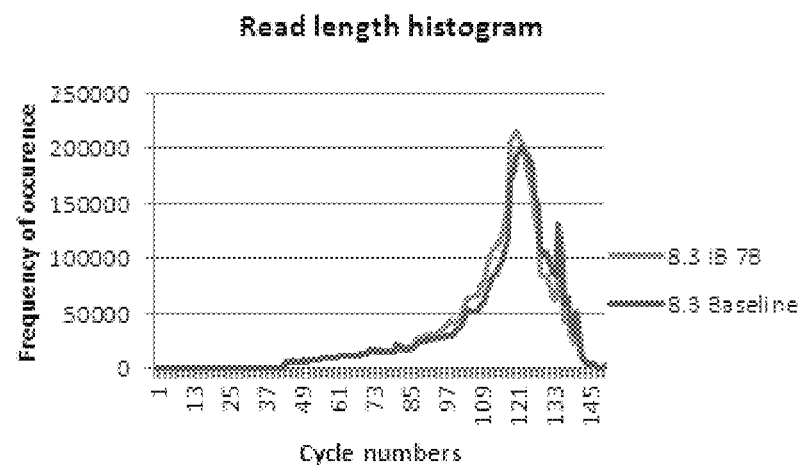
FIG. 3A-D presents exemplary data showing comparative read length distributions between a conventional imaging buffer and a Photoprotective imaging buffer 7B subsequent to each SBS run.
Figure 3B:
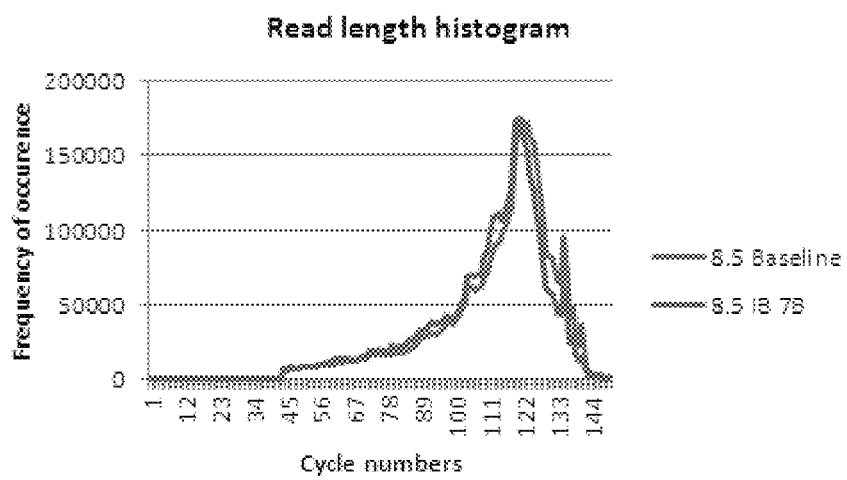
Figure 3C:
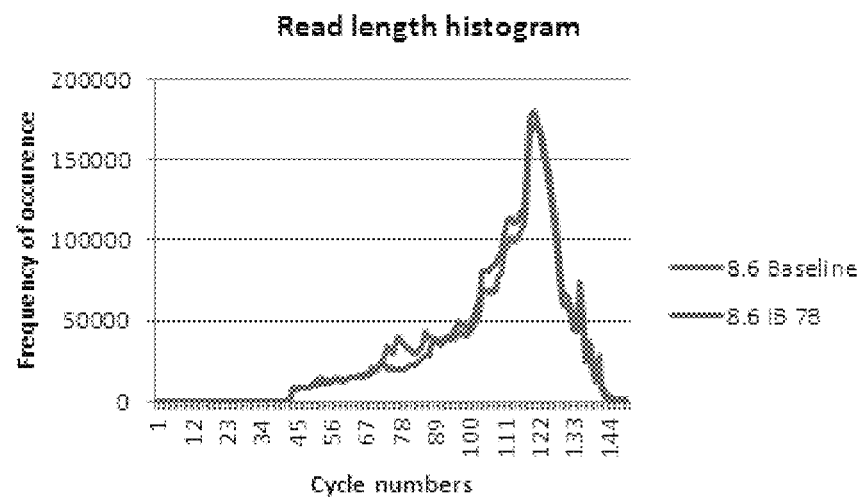
Figure 3D:
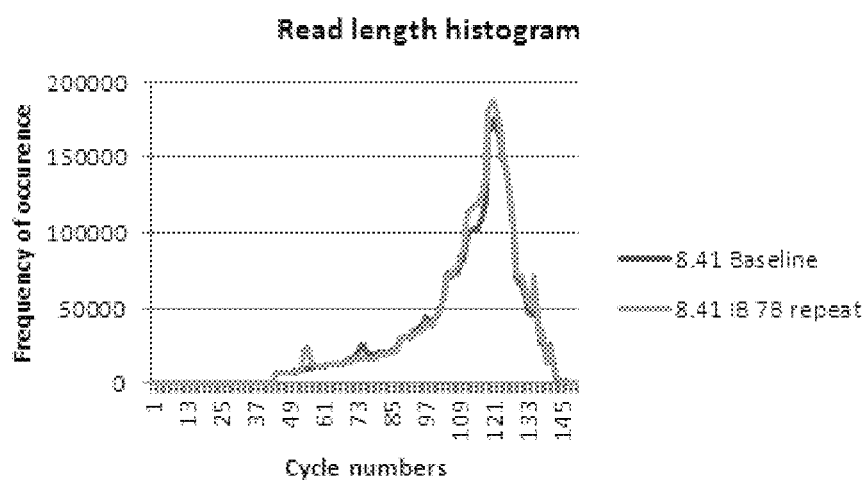
Figure 4A:
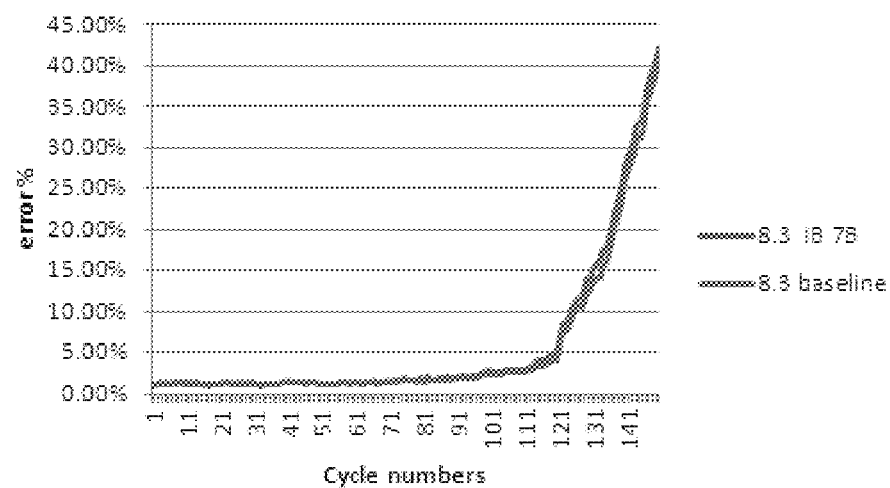
FIG. 4A-D presents exemplary data showing raw error plots between a conventional imaging buffer and a Photoprotective imaging buffer 7B subsequent to each SBS run.
Figure 4B:
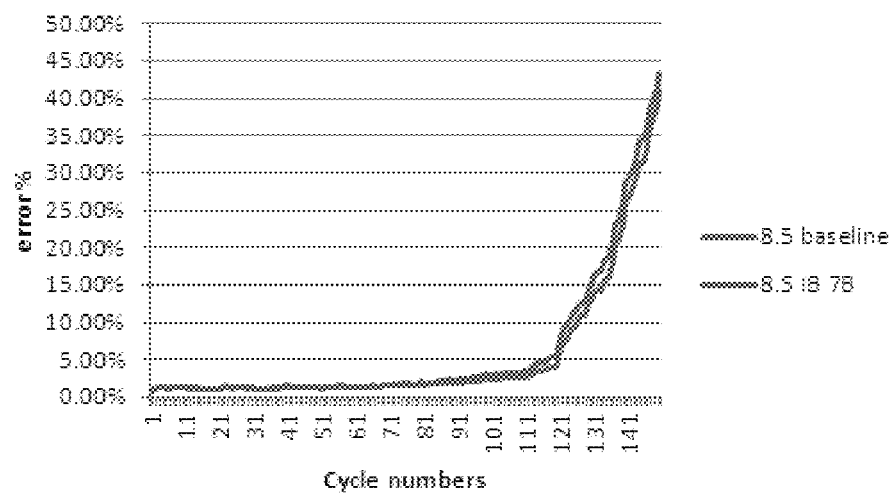
Figure 4C:
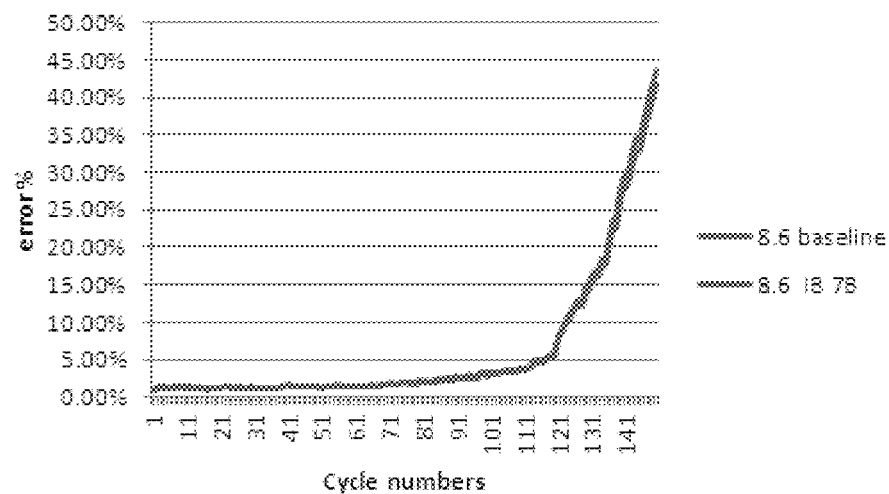
Figure 4D:
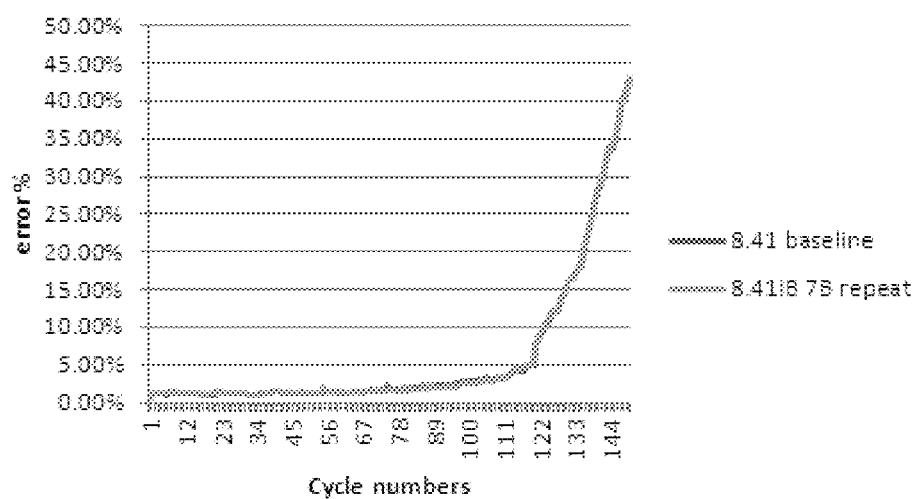

For example, GDP4 Testing was performed using the photoprotective imaging buffer reagent SC-P 7B made in accordance with Example II. The testing was run using an APF protocol v2 comprising 157 cycles and 130 tiles utilizing the SP101x gene panel. Of the four runs (e.g. 8.41) that was performed was deemed to be invalid and retested (noted as "**"). It can be seen that the conventional imaging reagent (Baseline IB) and a photoprotective imaging reagent SC-P 7B were comparable across all sequencing metrics. See, FIG. 2 and Table 1.

TABLE 1

Comparative Sequencing Metrics: Conventional IB (Baseline) versus SC-P 7B IB.

| Date | Run | GR | Sample ID | Output (MFST) | Beads/tiles | Error rate | % Live | % Mapped | % Polyclonal | % Perfect | AVG RL | Lead | Lag |
|---|---|---|---|---|---|---|---|---|---|---|---|---|---|
| Mar. 25, 2016 | IB 7B | 8.5 | SP101x | 1.77127963 | 429218.169 | 0.747583 | 48% | 29% | 36% | 0.5955009 | 103.6339 | 0.337969 | 0.1115 |
| Apr. 15, 2016 | IB 7B Retest** | 8.41 | SP101x | 1.904131381 | 428153.625 | 0.775358 | 50% | 31% | 35% | 0.5969785 | 110.6978 | 0.405625 | 0.084068 |
| Apr. 5, 2016 | IB 7B | 8.6 | SP101x | 1.87737536 | 440901.246 | 0.751118 | 49% | 30% | 34% | 0.5990981 | 108.7261 | 0.347992 | 0.098931 |
| Apr. 11, 2016 | IB 7B | 8.3 | SP101x | 2.052871269 | 444626.646 | 0.728655 | 51% | 31% | 35% | 0.6067697 | 113.2278 | 0.406538 | 0.117338 |
|  |  |  |  | 1.901 | 435729 | 0.75% | 49% | 30% | 35% | 59% | 110 | 0.374 | 0.102 |
| Mar. 28, 2016 | Baseline | 8.5 | SP101x | 1.852687368 | 434523.031 | 0.795124 | 48% | 29% | 36% | 0.5857853 | 112.4375 | 0.4325 | 0.123562 |
| Mar. 28, 2016 | Baseline | 8.41 | SP101x | 1.808064963 | 435729 | 0.77365 | 49% | 29% | 37% | 0.5958026 | 110.3599 | 0.424246 | 0.126323 |
| Apr. 8, 2016 | Baseline | 8.6 | SP101x | 1.890117702 | 438295.854 | 0.803485 | 51% | 31% | 36% | 0.583074 | 108.433 | 0.332785 | 0.187277 |
| Apr. 14, 2016 | Baseline | 8.3 | SP101x | 2.023612666 | 431433.115 | 0.778109 | 52% | 31% | 36% | 0.5949944 | 115.0466 | 0.409185 | 0.157954 |
|  |  |  |  | 1.893 | 434999 | 0.79% | 49% | 30% | 36% | 58% | 111 | 0.399 | 0.149 |

These data show that the metric, lag, shows the only statistically relevant difference between the two imaging reagents with a 30% lower lag when tested with a photoprotective imaging reagent SC-P 7B. The read length distributions among the four runs were equivalent when tested between the two imaging reagents. See, FIGS. 3A-3D. The raw error plots among the four runs were also equivalent when tested between the two imaging reagents. See, FIGS. 4A-4D.

Testing was also performed using various embodiments of the exemplary photoprotective imaging reagent 9CV2T made in accordance with Example III. Three different versions of the 9CV2T reagents were made. Although it is not necessary to understand the mechanism of an invention, it is believed that at least one of these reagents resulted in an improved signal retention. For example, three of the tested versions of 9CV2T imaging reagents comprised:

SC-P9 pH 8.5

| Tris | 50 mM |
|---|---|
| L-Carnitine | 50 mM |
| Trolox | 15 mM |
| Protocatechuic acid ethyl ester | 20 mM | or,

SC-P9B pH 8.5

| Tris | 50 mM |
|---|---|
| L-Carnitine | 15 mM |
| Trolox | 15 mM |
| Protocatechuic acid ethyl ester | 20 mM | and,
SC-P9C pH 8.5

| | |
|---|---|
| Tris | 50 mM |
| L-Carnitine | 15 mM |
| Trolox | 15 mM |
| Protocatechuic acid ethyl ester | 10 mM |

A comparison of basic sequencing metrics was made between these three SCRP version 9CV2T imaging reagents and the conventional IB reagent with a sequencing protocol of 137 cycles using a Vaccinia virus (VACV) strain TianTan TP03 genome. See, Table 2.

TABLE 2

Comparison of Sequencing Metrics Between SC-P Version 9 IBs And A Conventional IB (IB_Baseline).

| Run Name | GR/Sample | Output (MFST) | % Mapped | AVG RL | Error Rate (MFST) | % Perfect | Lead | Lag |
|---|---|---|---|---|---|---|---|---|
| IB_Baseline | 8.26/TP03 | 1.23E+09 | 32.6% | 99.5 | 0.60% | 67.6% | 0.421 | 0.125 |
| IB_SC-P9 | 8.26/TP03 | 1.21E+09 | 33.1% | 98.5 | 0.54% | 69.00% | 0.407 | 0.116 |
| IB_SC-P9B | 8.26/TP03 | 1.16E+09 | 31.8% | 98.9 | 0.54% | 69.1% | 0.389 | 0.124 |
| IB_SC-P9C | 8.17/TP03 | 1.12E+09 | 30.6% | 99.7 | 0.58% | 67.5% | 0.432 | 0.093 |

Figure 5:
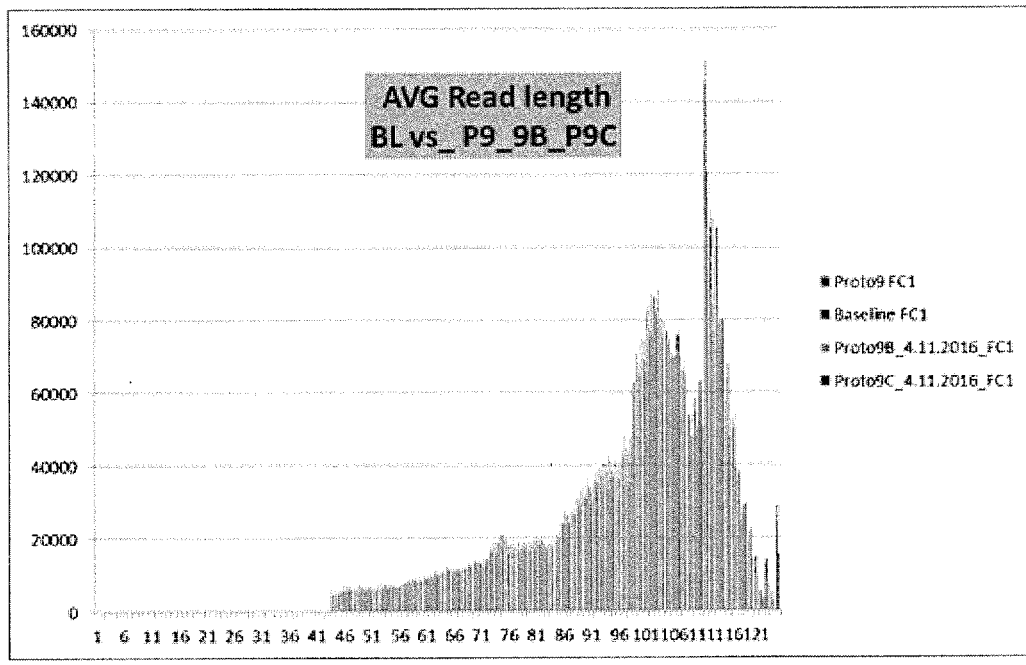
FIG. 5 presents exemplary data showing a comparison of average read length data between a conventional imaging buffer (IB_Baseline) and three (3) versions of a Photoprotective imaging buffer SC-P version 9.
Figure 6A:
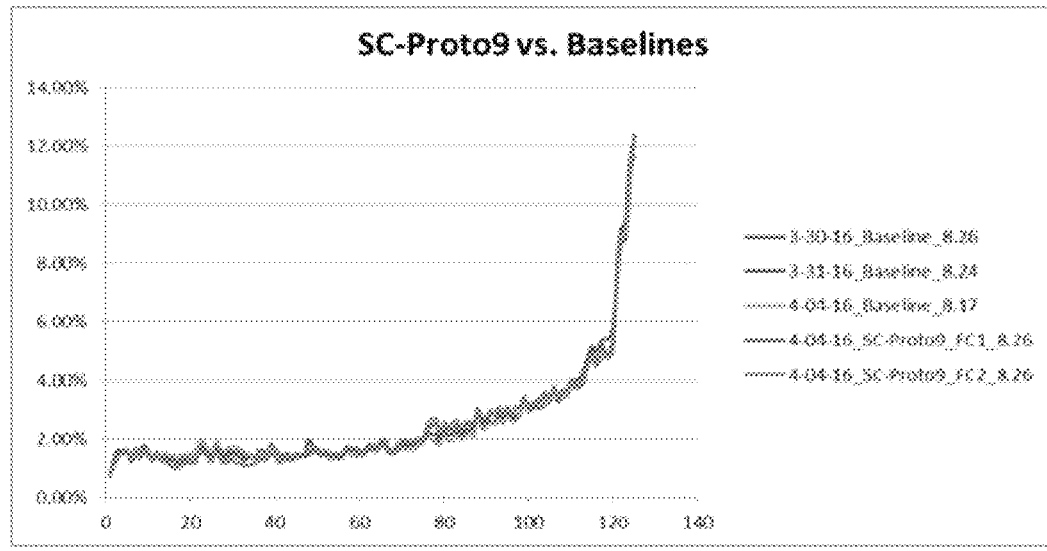
FIG. 6A-C presents exemplary data showing a comparison of raw error plot data between a conventional imaging buffer (IB_Baseline) and three (3) versions of a Photoprotective imaging buffer SC-P version 9.
Figure 6B:
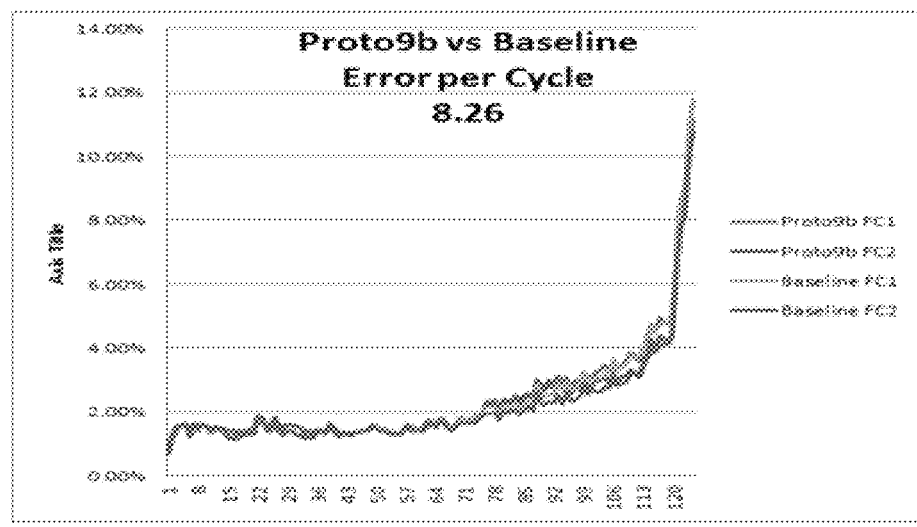
Figure 6C:
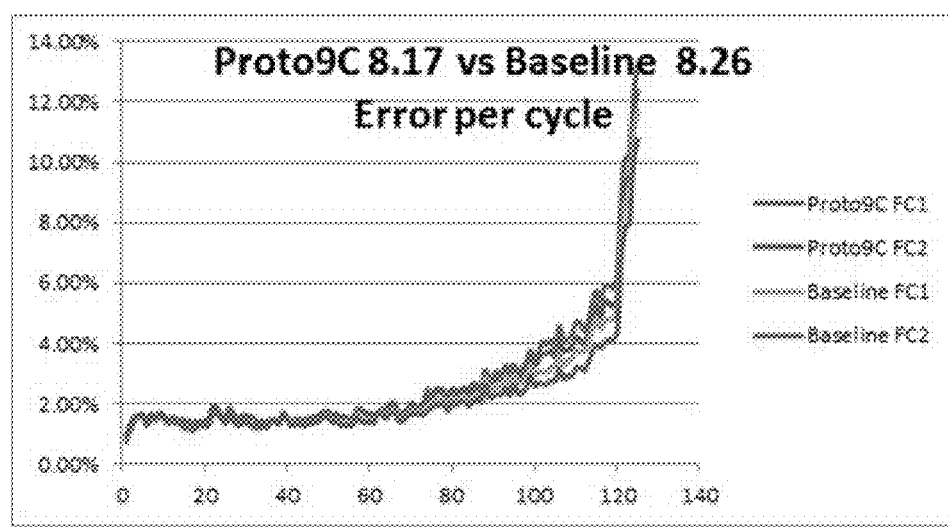
Figure 7:
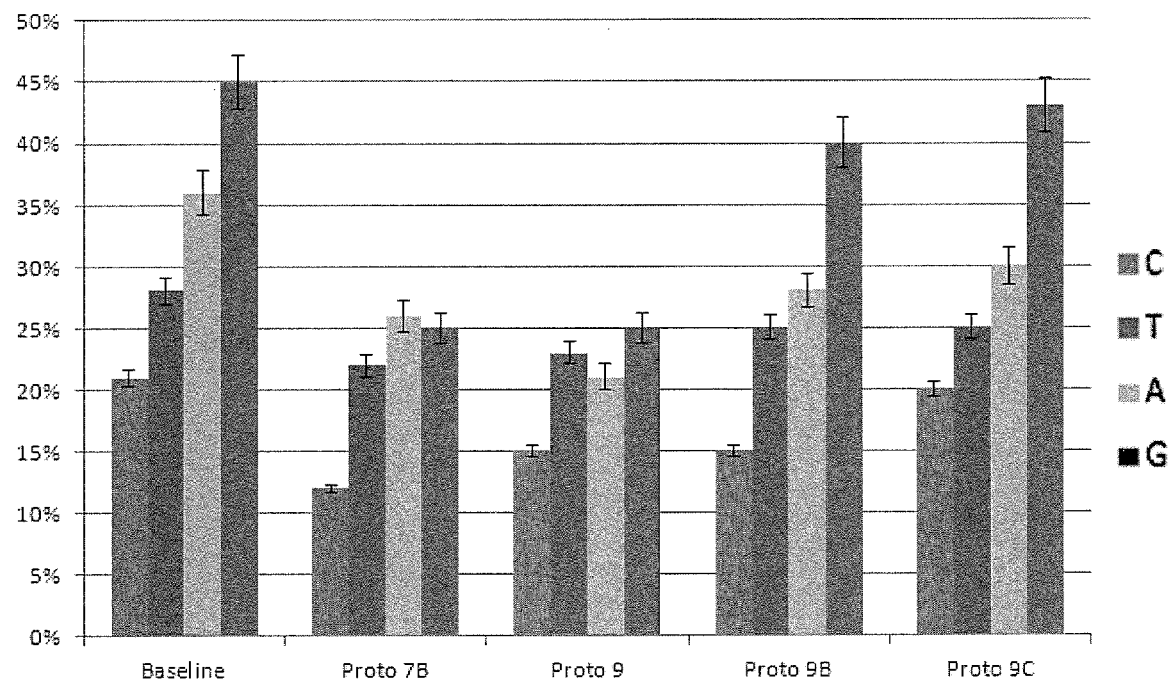
FIG. 7 presents exemplary data showing the effect of lower ionic and aromatic compound concentrations in an imaging buffer on nucleotide signal retention.

A relative equivalency was seen between these SC-P version 9CV2T imaging reagents and the baseline imaging reagent with respect to average read length. See, FIG. 5. Such equivalency was also observed for the raw data plots between the SC-P version 9CV2T imaging reagents and the baseline imaging reagent. See, FIGS. 6A-C. These data demonstrate that lowering of concentrations of ionic and aromatic compound (e.g., carnitine and protocatechuic acid, respectively), does improve signal retention. See, FIG. 7. Although it is not necessary to understand the mechanism of an invention, it is believed that this observation is likely due to mitigated signal quenching which usually arises from interactions between fluorophores and aromatic/ionic species in a photoprotective buffer.

The SC-P9C imaging reagent was used in a 157 cycles non-APF/88 tile protocol on a BRCA gene panel (runs 8.17; 8.24; 8.26). The sequencing metrics were compared to a reference imaging IB. See, Table 3.

TABLE 3

Sequence Metrics Comparison Of SC-P9C To Baseline IB On A BRCA Gene Panel

| Run Condition | GR | Run date | Type | Output (MFST) | Beads/tile | % Live | % Mapped | % Polyclonal | AVG RL | Error (MFST) | % Perfect | Lead | Lag |
|---|---|---|---|---|---|---|---|---|---|---|---|---|---|
| Baseline_BRCA | 8.17 | Apr. 15, 2016 | HG19 BRCA | 1.14E+09 | 426294 | 47% | 26% | 41% | 115.0 | 0.72% | 58% | 0.513 | 0.060 |
| Baseline_BRCA | 8.17 | Apr. 15, 2016 | HG19 BRCA | 1.17E+09 | 424933 | 45% | 27% | 38% | 114.0 | 0.74% | 57% | 0.466 | 0.091 |
| Prototype 9C_BRCA | 8.26 | Apr. 15, 2016 | HG19 BRCA | 1.09E+09 | 428096 | 44% | 26% | 36% | 110.0 | 0.78% | 53% | 0.477 | 0.061 |
| Prototype 9C_BRCA | 8.26 | Apr. 15, 2016 | HG19 BRCA | 1.14E+09 | 422093 | 45% | 26% | 36% | 112.0 | 0.79% | 54% | 0.446 | 0.084 |
| Prototype 9C_BRCA | 8.24 | Apr. 15, 2016 | HG19 BRCA | 1.15E+09 | 427948 | 43% | 25% | 35% | 110.0 | 0.82% | 51% | 0.444 | 0.072 |
| Prototype 9C_BRCA | 8.24 | Apr. 15, 2016 | HG19 BRCA | 1.18E+09 | 424163 | 43% | 26% | 35% | 113.0 | 0.87% | 52% | 0.454 | 0.082 |

Figure 8:
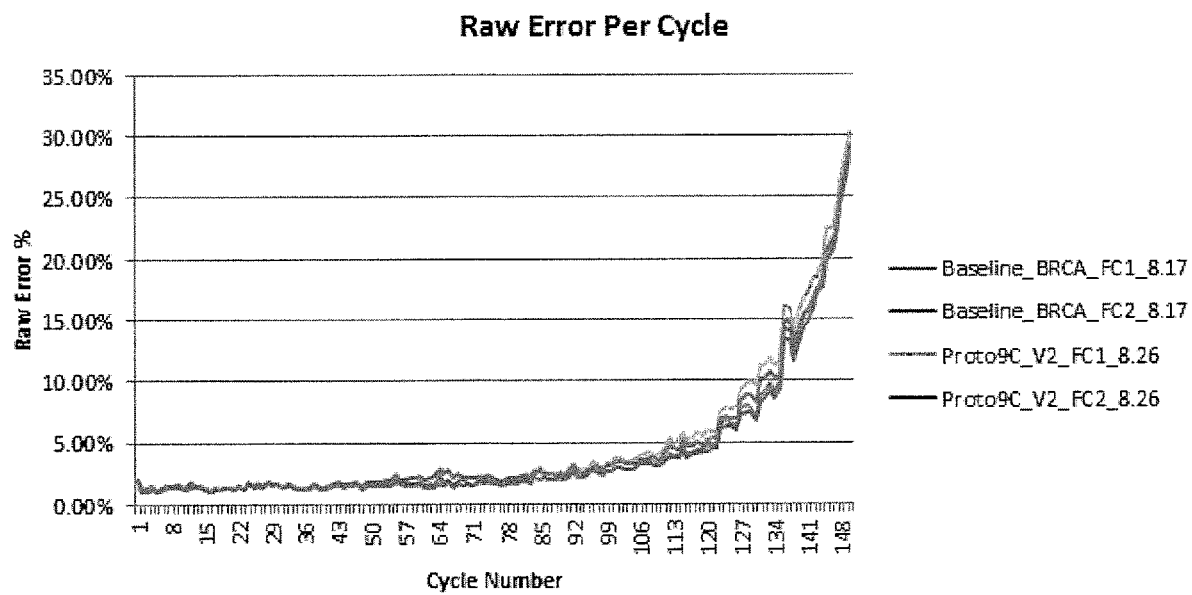
FIG. 8 presents exemplary data showing raw error rates in sequencing runs using SC-P9C imaging reagent versus a baseline IB.

A comparison of the raw error rates demonstrated equivalency between the two imaging reagents. See, FIG. 8. The SC-P9C imaging reagent sequencing metrics were also compared between the HEPES buffer and the TRIS buffer using a 157 cycles non-APF/88 the protocol on a DHMG02 BRCA gene panel. See, Table 4.

TABLE 4

Sequence Metrics Comparison Of SC-P9C To Baseline IB On A BRCA Gene Panel
Comparing HEPES Buffer To TRIS Buffer

| Run Condition | GR | Sample ID | Run date | Type | Cycles | Output (MFST) | Beads/tile |
|---|---|---|---|---|---|---|---|
| Ref_Baseline | 8.24 | FC1_DHMG02 | Apr. 26, 2016 | HG19 BRCA | 150 | 1.28E+09 | 419417 |
| Ref_Baseline | 8.24 | FC2_DHMG02 | Apr. 26, 2016 | HG19 BRCA | 150 | 1.34E+09 | 409874 |
| IB_P9CV2_HEPES | 8.26 | FC1_DHMG02 | Apr. 26, 2016 | HG19 BRCA | 150 | 1.37E+09 | 417428 |
| IB_P9CV2_HEPES | 8.26 | FC2_DHMG02 | Apr. 26, 2016 | HG19 BRCA | 150 | 1.35E+09 | 423869 |
| Proto9C_V2_Tris | 8.26 | FC1_DHMG02 | Apr. 15, 2016 | HG19 BRCA | 150 | 1.07E+09 | 428096 |
| Proto9C_V2_Tris | 8.26 | FC2_DHMG02 | Apr. 15, 2016 | HG19 BRCA | 150 | 1.10E+09 | 422093 |
| Proto9C_V2_Tris | 8.24 | FC1_DHMG02 | Apr. 15, 2016 | HG19 BRCA | 150 | 1.03E+09 | 427948 |
| Proto9C_V2_Tris | 8.24 | FC2_DHMG02 | Apr. 15, 2016 | HG19 BRCA | 150 | 1.08E+09 | 424163 |

| Run Condition | % Live | % Mapped | % Polyclonal | AVG RL | Error (MFST) | % Perfect | Lead | Lag |
|---|---|---|---|---|---|---|---|---|
| Ref_Baseline | 51% | 31% | 36% | 110.8 | 0.83% | 56% | 0.490 | 0.024 |
| Ref_Baseline | 53% | 33% | 36% | 113.2 | 0.83% | 56% | 0.490 | 0.035 |
| IB_P9CV2_HEPES | 49% | 31% | 35% | 112.6 | 0.79% | 57% | 0.420 | 0.040 |
| IB_P9CV2_HEPES | 50% | 32% | 35% | 114.5 | 0.76% | 58% | 0.449 | 0.046 |
| Proto9C_V2_Tris | 44% | 26% | 36% | 109.0 | 0.96% | 51% | 0.477 | 0.061 |
| Proto9C_V2_Tris | 45% | 26% | 36% | 111.5 | 0.94% | 52% | 0.446 | 0.084 |
| Proto9C_V2_Tris | 43% | 25% | 35% | 108.7 | 1.03% | 50% | 0.444 | 0.072 |
| Proto9C_V2_Tris | 43% | 26% | 35% | 112.3 | 1.02% | 50% | 0.454 | 0.082 |

Figure 9A:
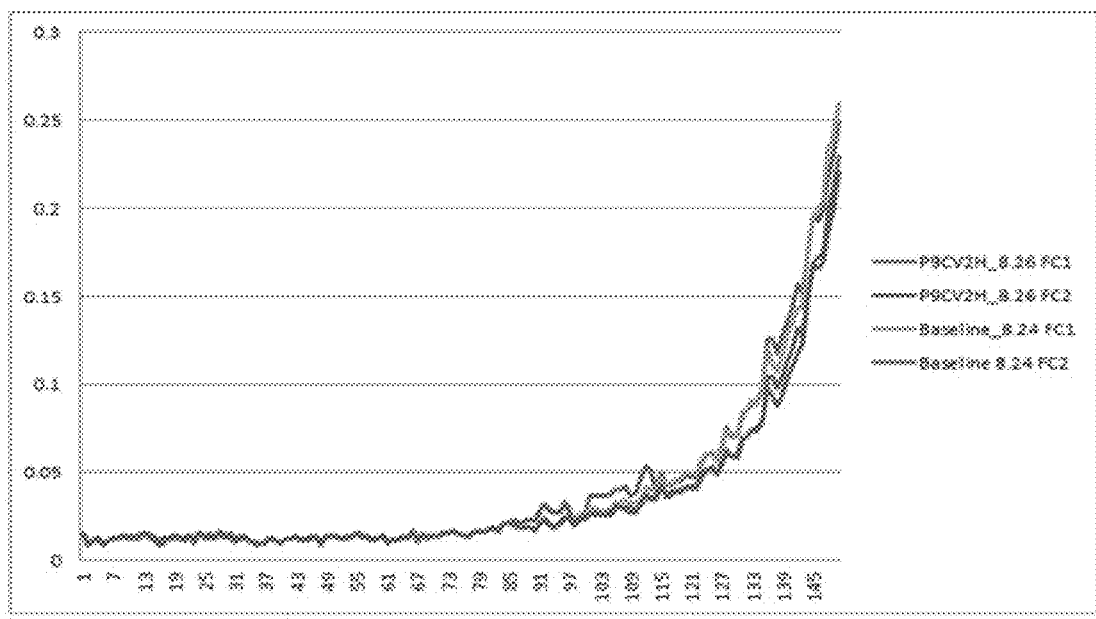
FIG. 9A-B presents exemplary data showing raw error rates in sequencing runs using SC-P9C imaging reagent formulated with either a HEPES buffer or a TRIS buffer versus a baseline IB.
Figure 9B:
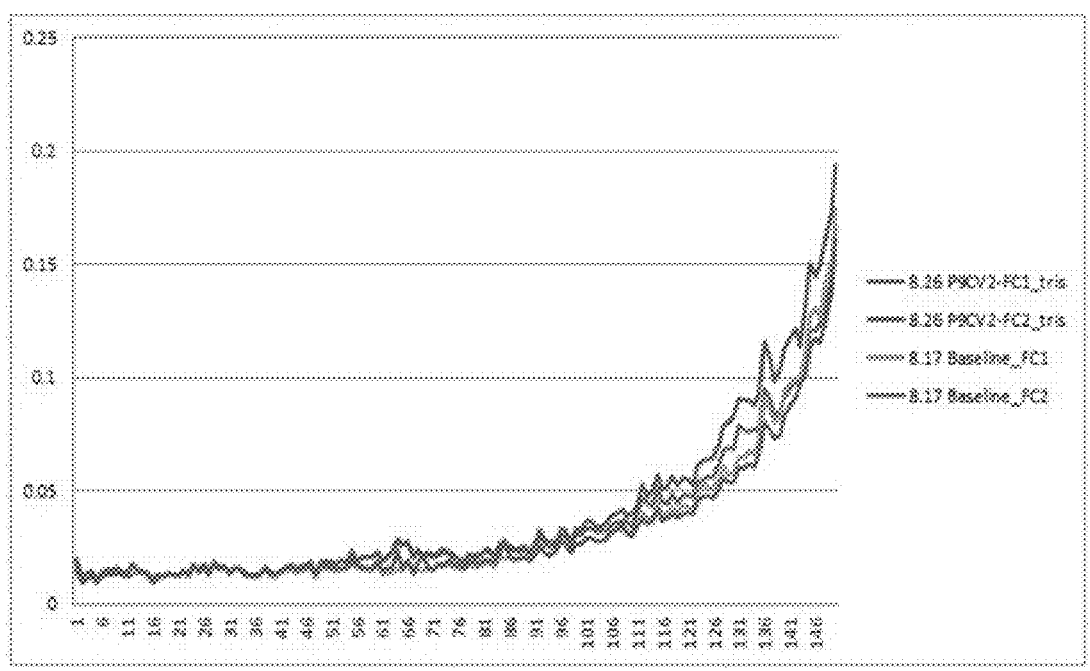

The data demonstrate that the SC-P 9C imaging reagent formulated in a HEPES buffer outperforms the SC-P 9C imaging reagent formulated in Tris HCl. Similarly, the raw error rate is less using a HEPES buffer as compared to a Tris HCl and is more similar to the baseline IB. See, FIGS. 9A and 9B.

These data demonstrate that photoprotective imaging reagents with protocatechuic ethyl ester is superior to photoprotective imaging reagents with gentisic acid in regards to signal stability and quality. Although it is not necessary to understand the mechanism of an invention, it is believed that signal stability and quality plays a role in sequencing performance quality. Nonetheless, both gentisic- and protocatechuic-based cocktail chemistries (i.e., SC-P 7B and SC-P 9C, respectively) are expected to benchmark competitively in regards to comparative performance for long read sequencing. From a manufacturing perspective, however, photoprotective imaging reagents with protocatechuic ethyl ester may be preferable than photoprotective imaging reagents with gentisic acid due to better flexibility and cost effectiveness of making the formulation.

Further studies were performed to determine if decreasing carnitine concentration in a photoprotective imaging reagent (e.g., between approximately 50 mM to 5 mM) influences sequencing performance. The composition of the tested photoprotective carnitine imaging reagents (e.g., SC-P9, SC-P9B and SC-P9C) are as follows:

Prototype 9

| | |
|---|---|
| 50 mM | Tris buffer pH 8.5 |
| 50 mM | L-Carnitine |

-continued

| | |
|---|---|
| 15 mM | Trolox |
| 20 mM | Protocatechuic Acid Ethyl Ester |

Prototype 9B

| | |
|---|---|
| 50 mM | Tris buffer pH 8.5 |
| 15 mM | L-Carnitine |
| 15 mM | Trolox |
| 20 mM | Protocatechuic Acid Ethyl Ester |

Prototype 9D

| | |
|---|---|
| 50 mM | Tris buffer pH 7.8 |
| 5 mM | L-Carnitine |
| 15 mM | Trolox |
| 20 mM | Protocatechuic Acid Ethyl Ester |

The sequencing runs (8.17, 8.24, 8.26) setups comprised 132 cycles for both the reference and/or baseline IB reagent and the photoprotective IB reagent using samples NA12878/101X (ID: TP03) or NA12878/BRCA (ID: DHMG02). The data show that 15 mM Carnitine is provides an optimal working concentration based on average read length and signal retention. See, Table 5.

TABLE 5

ADAM Results From Carnitine Concentration Analysis

| Run Condition | GR | Sample ID | Run date | Type | Cycles | Output (MFST) | Beads/tile | % Live |
|---|---|---|---|---|---|---|---|---|
| IB_baseline_8.26_FC1 | 8.26 | TP03_FC1 | Mar. 30, 2016 | HG19 101X | 125 | 1.18E+09 | 446379.5 | 48.8% |
| IB_baseline_8.26_FC2 | 8.26 | TP03_FC2 | Mar. 30, 2016 | HG19 101X | 125 | 1.20E+09 | 414836.1 | 51.2% |
| IB_baseline_8.17_FC1 | 8.17 | FC1_TP03 | Apr. 4, 2016 | HG19 101X | 125 | 1.27E+09 | 426583.5 | 53.6% |
| IB_baseline_8.17_FC2 | 8.17 | FC2_TP03 | Apr. 4, 2016 | HG19 101X | 125 | 1.26E+09 | 426191.8 | 52.7% |
| IB_SC-P9_FC1 | 8.26 | FC1_TP03 | Apr. 4, 2016 | HG19 101X | 125 | 1.21E+09 | 424152.8 | 52.4% |

TABLE 5-continued

ADAM Results From Carnitine Concentration Analysis

| | | | | | | | | |
|---|---|---|---|---|---|---|---|---|
| IB_SC-P9_FC2 | 8.26 | FC2_TP03 | Apr. 4, 2016 | HG19 101X | 125 | 1.22E+09 | 432521.2 | 52.8% |
| IB_SC-P9B_FC1 | 8.26 | FC1_TP03 | Apr. 11, 2016 | HG19 101X | 125 | 1.16E+09 | 419886.9 | 49.6% |
| IB_SC-P9B_FC2 | 8.26 | FC2_TP03 | Apr. 11, 2016 | HG19 101X | 125 | 1.16E+09 | 414822.6 | 49.9% |
| Baseline_BRCA_AGR | 8.17 | 1_DHMGO | Apr. 15, 2016 | HG19 BRCA | 125 | 1.01E+09 | 426294.1 | 47.1% |
| Baseline_BRCA_AGR | 8.17 | 2_DHMGO | Apr. 15, 2016 | HG19 BRCA | 125 | 1.03E+09 | 424932.8 | 45.1% |
| IB_Proto90_BRCA_AGR | 8.26 | 1_DHMGO | Apr. 19, 2016 | HG19 BRCA | 125 | 9.85E+09 | 428784.6 | 44.9% |
| IB_Proto90_BRCA_AGR | 8.26 | 2_DHMGO | Apr. 19, 2016 | HG19 BRCA | 125 | 1.02E+09 | 430237.1 | 45.6% |

| Run Condition | % BC | % mapped | G Read Leag | Error Rate | % Perfect | Lead | Lag | Notes |
|---|---|---|---|---|---|---|---|---|
| IB_baseline_8.26_FC1 | 73.0% | 30.5% | 99.0 | 0.55% | 69.1% | 0.415 | 0.139 | baseline 101X |
| IB_baseline_8.26_FC2 | 73.6% | 32.5% | 100.9 | 0.54% | 69.3% | 0.378 | 0.149 | baseline 101X |
| IB_baseline_8.17_FC1 | 74.3% | 34.1% | 99.4 | 0.58% | 67.6% | 0.470 | 0.109 | baseline 101X |
| IB_baseline_8.17_FC2 | 73.6% | 33.2% | 100.6 | 0.59% | 66.6% | 0.423 | 0.127 | baseline 101X |
| IB_SC-P9_FC1 | 74.8% | 33.0% | 97.9 | 0.53% | 69.7% | 0.409 | 0.111 | 50 mM carnitine |
| IB_SC-P9_FC2 | 75.0% | 33.1% | 97.0 | 0.56% | 68.3% | 0.405 | 0.122 | 50 mM carnitine |
| IB_SC-P9B_FC1 | 73.3% | 31.7% | 93.6 | 0.55% | 69.0% | 0.389 | 0.126 | 15 mM carnitine |
| IB_SC-P9B_FC2 | 73.5% | 31.9% | 99.2 | 0.54% | 69.2% | 0.383 | 0.123 | 15 mM carnitine |
| Baseline_BRCA_AGR | 71% | 26% | 103.5 | 0.68% | 64.4% | 0.473 | 0.109 | baseline_BRCA |
| Baseline_BRCA_AGR | 72% | 27% | 104.1 | 0.70% | 63.2% | 0.431 | 0.117 | baseline_BRCA |
| IB_Proto90_BRCA_AGR | 71% | 27% | 97.2 | 0.69% | 63.6% | 0.425 | 0.101 | 5 mM carnitine |
| IB_Proto90_BRCA_AGR | 71% | 27% | 99.0 | 0.68% | 63.5% | 0.425 | 0.111 | 5 mM carnitine |

Figure 10:
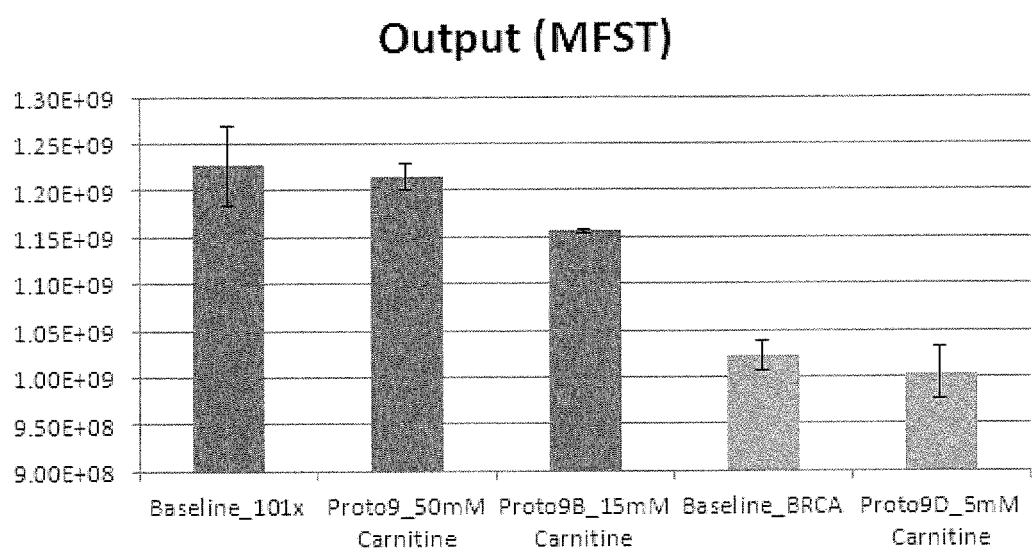
FIG. 10 presents exemplary data showing the effects of carnitine concentration on MFST data output in both 101x gene panels (blue) and BRCA gene panels (red).
Figure 11:
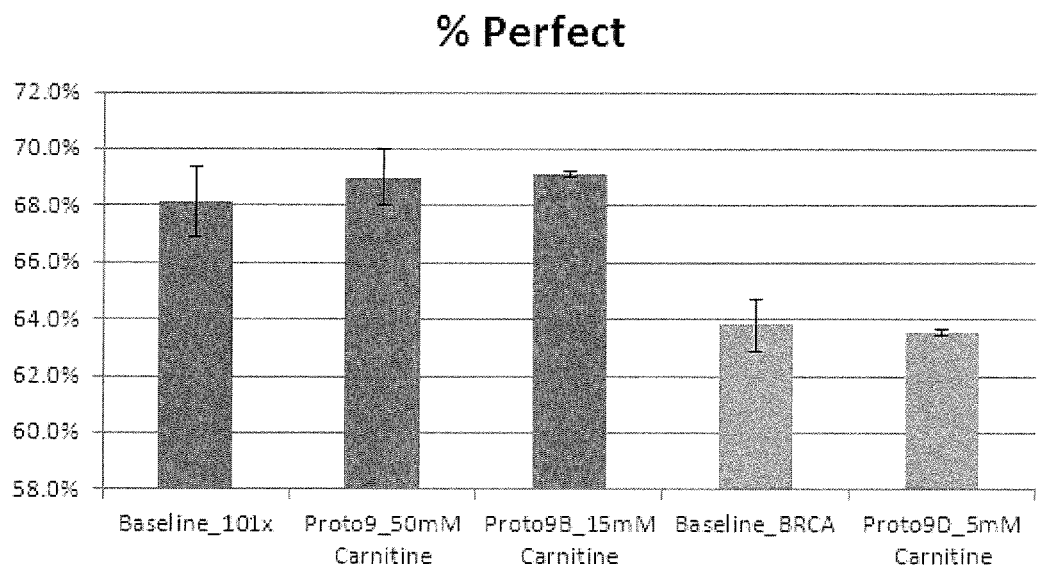
FIG. 11 presents exemplary data showing the effects of carnitine concentration on percent perfect parameters in both 101x gene panels (blue) and BRCA gene panels (red).
Figure 12:
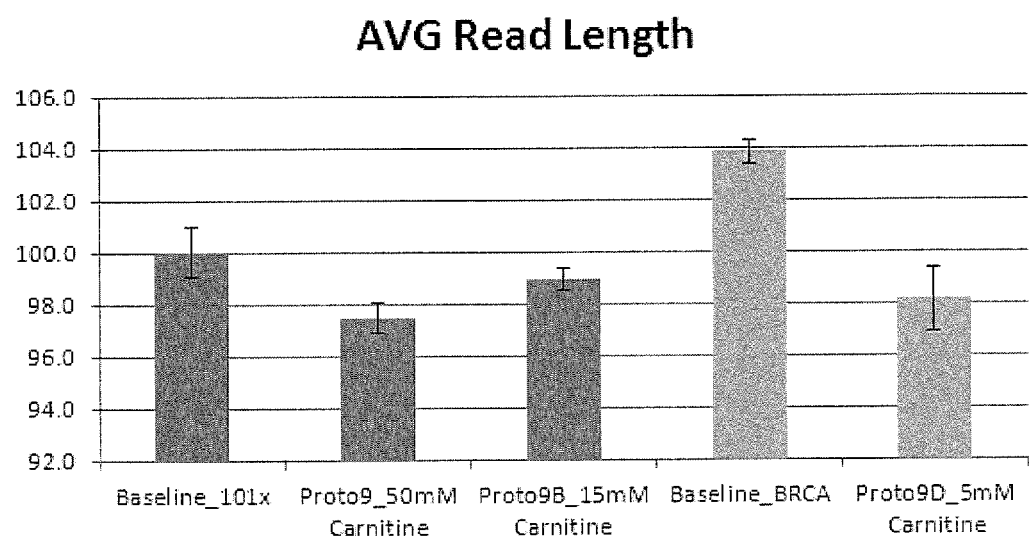
FIG. 12 presents exemplary data showing the effects of carnitine concentration on average read length in both 101x gene panels (blue) and BRCA gene panels (red).
Figure 13:
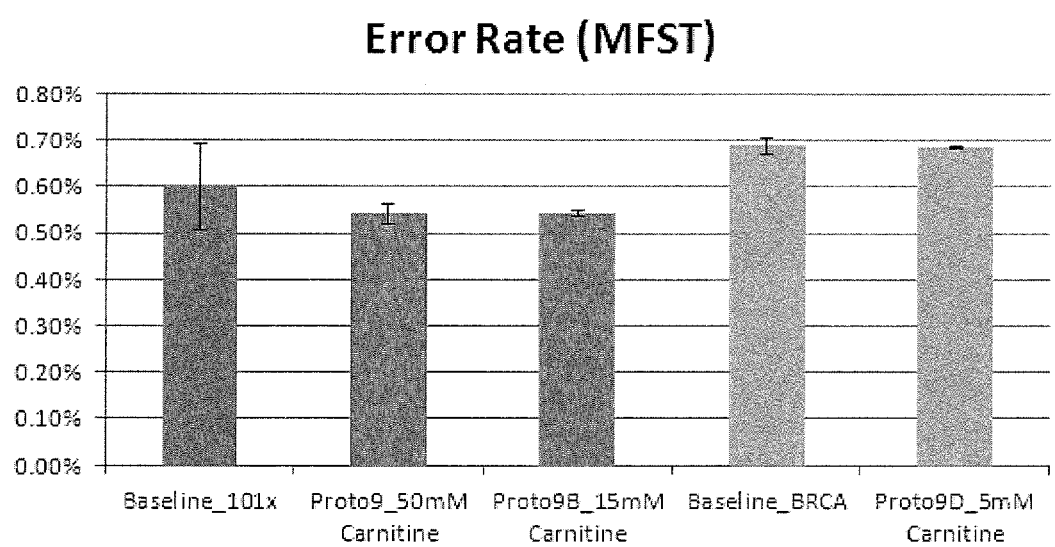
FIG. 13 presents exemplary data showing the effects of carnitine concentration on percent error rate in both 101x gene panels (blue) and BRCA gene panels (red).
Figure 14A:
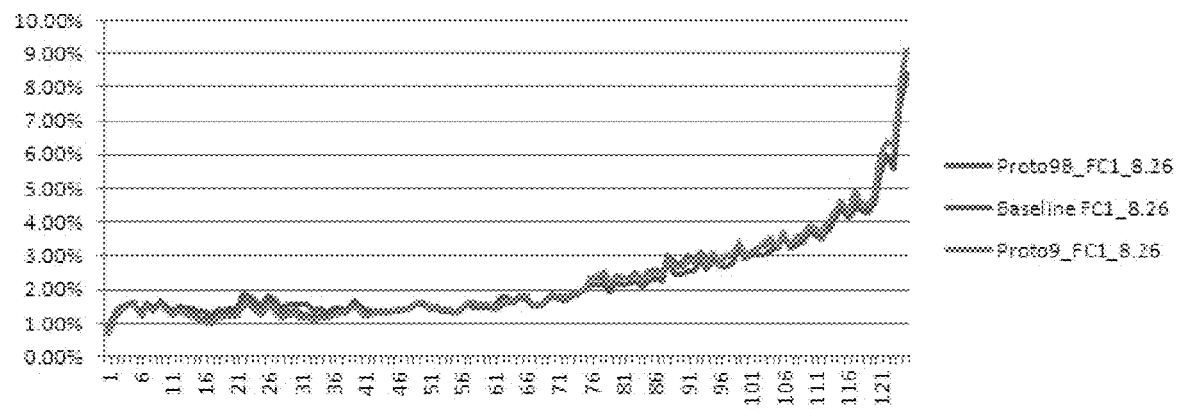
FIG. 14A-B presents exemplary data showing the effects of carnitine concentration on raw error rate in both 101x gene panels (blue) and BRCA gene panels (red).
Figure 14B:
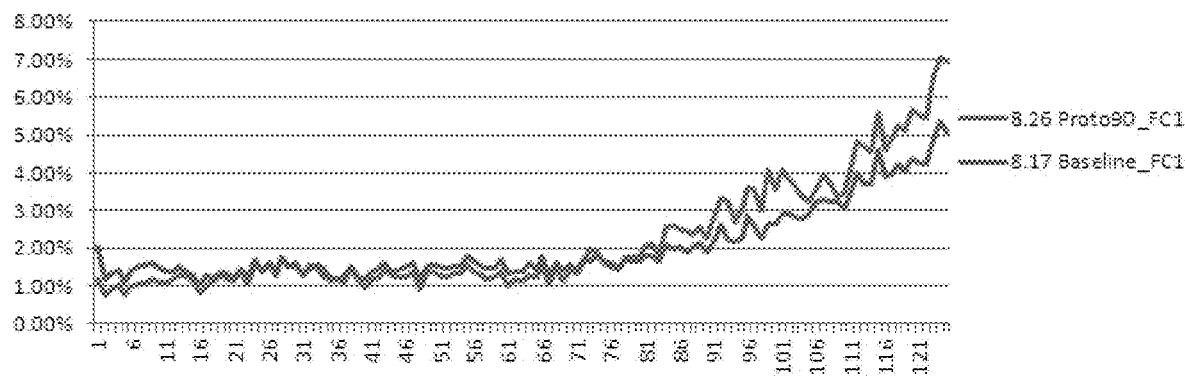
Figure 15A:
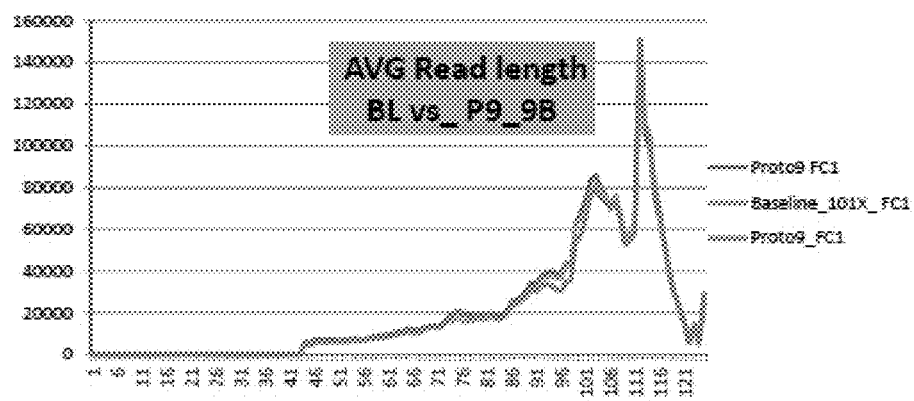
FIG. 15A-B presents exemplary data showing the effects of carnitine concentration on read length distribution in both 101x gene panels (blue) and BRCA gene panels (red).
Figure 15B:
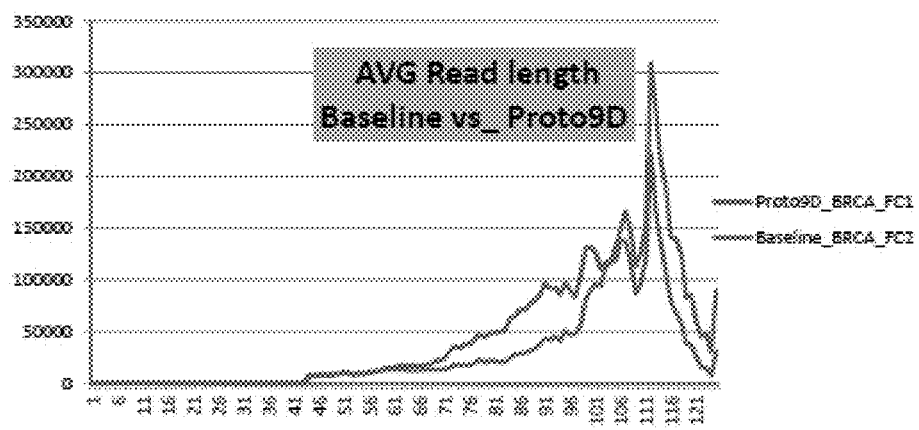
Figure 16:
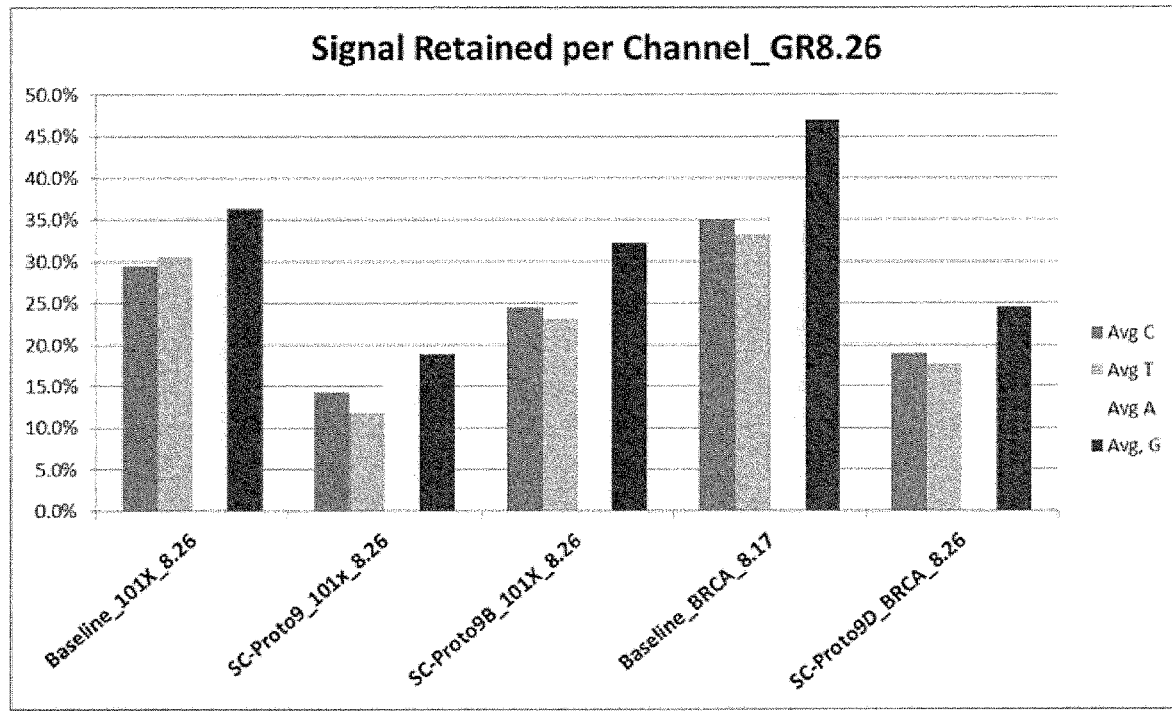
FIG. 16 presents exemplary data showing the effects of carnitine concentration on nucleotide signal retention in both 101x gene panels (blue) and BRCA gene panels (red).

In particular, reduced carnitine concentration lowers data output (MFST) in a concentration-dependent manner in both the 101x gene panel and the BRCA gene panel. See, FIG. 10. This output data was collected under conditions where the percent perfect parameters went unchanged as compared to the reference IB reagent. See, FIG. 11. The average read length, however, was seen to be lower overall when the photoprotective imaging reagents contain carnitine. See, FIG. 12. Nonetheless, there was no effect of photoprotective imaging reagents containing carnitine on percent error rate when compared to the reference IB reagent. See, FIG. 13. There were differences, however, between photoprotective imaging reagents having different carnitine concentrations regarding the raw error rate parameter. For example, the SC-9 IB reagent (50 mM carnitine) and SC-9B IB reagent (15 mM carnitine) had raw error rates similar to the reference IB reagent. See, FIG. 14A. The SC-9D IB reagent (5 mM carnitine), however, showed a higher raw error rate as compared to the reference IB reagent. See, FIG. 14B. This data pattern is seen for the distribution of read lengths between the tested imaging reagents. The SC-9 IB reagent (50 mM carnitine) and SC-9B IB reagent (15 mM carnitine) had read length distributions that were similar to the reference IB reagent. See, FIG. 15A. The SC-9D IB reagent (5 mM carnitine), however, showed a read length distribution that was biased to the early cycles, and somewhat lower, as compared to the reference IB reagent. See, FIG. 15B. Signal retention for all nucleotides was reduced in the presence of carnitine, as shown by the best signal retention with the lower carnitine concentration photoprotective IB reagent (e.g., SC-9B, 15 mM). See, FIG. 16.

Overall, the data presented herein shows that photoprotective SC-P 7B IB reagent and SC-P 9C IB reagent perform similarly to a conventional imaging buffer reagent (e.g., baseline IB) and deliver an average read length minimum requirement that is compatible with state of the art gene readers. Specifically, the data show that photoprotective imaging buffer reagents as contemplated herein are efficient when scanning an average read length of approximately 110 bp as compared to the optimal scanning range of state of the art gene readers of between approximately 110-130 bp.

EXPERIMENTAL

Example I

Photoprotective Imaging Formulation Stability and Preservation

Components in various photoprotective imaging mixtures as described herein have been tested for solubility and stability against precipitation and discoloration in imaging solution formulation using iris Ha as the base buffer. The optimal concentration windows for the various components have been found to be the following: Carnitine (5-50 mM); Trolox (5-15 mM); 2,5-Dihydroxybenzoic Acid (10-50 mM); and 3,4-Dihydroxybenzoic Acid Ethyl Ester (Protocatechuate Ethyl Ester)(10-20 mM).

Example II

Composition and Formulation of Photoprotective Imaging Reagent SC-P 7B

The following example describes the preparation of approximately two hundred (200) milliliters of imaging reagent that would be expected to support a 4FC/157 cycle SBS method.

50 mM Tris buffer: 121.4 g/mol=1.21 g (Sigma: Cat #T1378-1kg)
50 mM L Carnitine: 197.66 g/mol=1.98 g (Sigma: Cat #C02133-100G)
15 mM Trolox: 250.29 g/mol=0.75 g (Sigma: Cat #238813-5G)
50 mM Gentisic Acid 176.1 g/mol=1.76 g (Sigma: G5129-10G)

1. Dissolve Tris Base in 180 mL milliQ water.
2. Add Trolox to the Tris buffer from Step 1.
3. Add L Carnitine to the above solution.
4. Add Gentisic acid sodium salt hydrate and dissolve.
5. Checked pH: ~4
6. Adjusted pH to 7.8 with 10M NaOH solution,
7. Bring total volume to 200 mL with milliQ water.
8. Filter sterilize.

9. Split imaging buffer into 2 conical tubes (approx. 25 mL aliquots each) for single FC GR run.

Example III

Composition and Formulation of Photoprotective Imaging Reagent 9CV2T

The following example describes the preparation of approximately two hundred (200) milliliters of imaging reagent.
50 mM Tris buffer: 121.4 g/mol=0.607 (Sigma: Cat #T1378-1kg)
15 mM L Carnitine: 197.66 g/mol=0.296 g (Sigma: Cat #C0238-100G)
15 mM Trolox: 250.29 g/mol=0.375 g (Sigma: Cat #238813-5G)
10 mM Protocatechuic Acid Ethyl Ester 182.17 g/mol=182.17 mg milligrams (Sigma: Cat #E24859-5G)
1. Dissolve Tris Base in 75 mL milliQ water.
2. Add Trolox and dissolve completely
3. Added Protocatechuic Acid
4. Add L Carnitine and dissolve completely.
5. Checked pH:
6. Adjusted pH to 8.5 with 10M NaOH.
7. Optional: Sonicate until well mixed.
8. Bring total volume to 100 mL with milliQ water.
9. Filter sterilize.

Example IV

Composition and Formulation of Photoprotective Imaging Reagent 9CV2H

The following example describes the preparation of approximately one hundred (100) milliliters of imaging reagent.
100 mM HEPES: 238.3 gr/mole=2.39 g (Sigma: Cat #H4034)
15 mM L Carnitine: 197.66 g/mol=0.296 g (Sigma: Cat #C0283-100G)
15 mM Trolox: 250.29 g/mol=0.375 g (Sigma: Cat #238813-5G)
10 mM Protocatechuic Acid Ethyl Ester 182.17 g/mol=0.182 g (Sigma: Cat #E24859-5G)
1 Liter 100 mM HEPES
219 gr HEPES
Dissolve in MilliQ water—final volume 1 Liter
pH was adjusted to 7.0.
1. Obtain 75 mL HEPES buffer (see below).
2. Add Trolox and dissolve completely
3. Added Protocatechuic Acid.
4. Add L Carnitine and dissolve completely.
5. Checked pH: ~5
6. Adjusted pH to 7.5 with 10M NaOH.
7. Optional: Sonicate until well mixed.
8. Bring total volume to 100 mL with milliQ water.
9. Filter sterilize.

We claim:

1. A method of incorporating labeled nucleotides, comprising:
    a) providing;
        i) a plurality of nucleic acid primers and template molecules,
        ii) a polymerase,
        iii) a first imaging reagent comprising a mixture of at least one fluorescence quenching inhibitor, at least one antioxidant, and at least one radical scavenger compound, and
        iv) a plurality of nucleotide analogues wherein at least a portion of said nucleotide analogues is labeled with a label attached through a cleavable linker to the base;
    b) hybridizing at least a portion of said primers to at least a portion of said template molecules so as to create hybridized primers;
    c) incorporating a first labeled nucleotide analogue with said polymerase into at least a portion of said hybridized primers so as to create extended primers comprising an incorporated labeled nucleotide analogue; and
    d) imaging said incorporated labeled nucleotide analogue in the presence of said first imaging reagent.

2. The method of claim 1, wherein said at least one fluorescence quenching inhibitor is 6-hydroxy-2,5,7,8-tetramethylchroman-2-carboxylic acid.

3. The method of claim 1, wherein said at least one antioxidant is selected from the group consisting of gentisic acid, protocatechuic acid and protocatechuate ethyl ester.

4. The method of claim 1, wherein said at least one radical scavenger compound is carnitine.

5. The method of claim 1, further comprising step (e) incorporating a second nucleotide analogue with said polymerase into at least a portion of said extended primers.

6. The method of claim 1, wherein said label is fluorescent.

7. An imaging reagent comprising:
    i) 2-Amino-2-hydroxymethyl-propane-1,3-diol (TRIS) HCl buffer;
    ii) carnitine ranging in concentration between approximately 5-50 mM;
    iii) 6-hydroxy-2,5,7,8-tetramethylchroman-2-carboxylic acid ranging in concentration between approximately 5-15 mM;
    iv) 2,5 dihydroxybenzoic acid ranging in concentration between approximately 10-50 mM; and
    v) 3,4, dihydroxybenzoic acid ethyl ester ranging in concentration between approximately 10-20 mM.

8. The method of claim 1, wherein said at least one antioxidant comprises gentisic acid, said at least one radical scavenger compound comprises carnitine, and said at least one fluorescence quenching inhibitor comprises 6-hydroxy-2,5,7,8-tetramethylchroman-2-carboxylic acid.

9. The method of claim 1, wherein said at least one antioxidant comprises protocatechuic acid ethyl ester, said at least one radical scavenger compound comprises carnitine, and said at least one fluorescence quenching inhibitor comprises 6-hydroxy-2,5,7,8-tetramethylchroman-2-carboxylic acid.

10. The method of claim 1, wherein said imaging delivers an average read length that is substantially similar to a read length obtained when said first imaging reagent is replaced by a second imaging reagent comprising 4-(2-hydroxyethyl)-1-piperazineethanesulfonic acid (HEPES) buffer, glucose oxidase, glucose, and 6-hydroxy-2,5,7,8-tetramethylchroman-2-carboxylic acid.

* * * * *